United States Patent
Malfait

(10) Patent No.: US 12,362,072 B2
(45) Date of Patent: Jul. 15, 2025

(54) CODE GENERATOR FOR CLINICAL RESEARCH STUDY SYSTEMS

(71) Applicant: Nurocor, Inc., Austin, TX (US)

(72) Inventor: Frederik Malfait, Wolfenschiessen (CH)

(73) Assignee: Nurocor, Inc., Austin, TX (US)

( * ) Notice: Subject to any disclaimer, the term of this patent is extended or adjusted under 35 U.S.C. 154(b) by 410 days.

(21) Appl. No.: 17/818,239

(22) Filed: Aug. 8, 2022

(65) Prior Publication Data

US 2024/0047080 A1 Feb. 8, 2024

(51) Int. Cl.
 *G16H 70/20* (2018.01)
 *G16H 10/20* (2018.01)
(52) U.S. Cl.
 CPC ............. *G16H 70/20* (2018.01); *G16H 10/20* (2018.01)
(58) Field of Classification Search
 CPC ............................... G16H 70/20; G16H 10/20
 See application file for complete search history.

(56) References Cited

U.S. PATENT DOCUMENTS 10,878,064 B2 12/2020 Burns et al.
12,007,870 B1* 6/2024 Jain ..................... G06F 11/3438
2019/0286620 A1 9/2019 Al-Haimi et al.
2024/0062854 A1* 2/2024 Ikeguchi ................ G16H 15/00

OTHER PUBLICATIONS

Ngouongo, Elsevier, 2013, pp. 318-327.*
Sinaci, Elsevier, 2013, pp. 784-794.*
"Reusable Asset Specification, Version 2.2," Object Management Group (OMG), accessed from https://www.omg.org/spec/RAS/2.2/PDF, Nov. 2005, 121 pp.
International Search Report and Written Opinion of International Application No. PCT/US2023/071685 dated Dec. 7, 2023, 10 pp.

* cited by examiner

*Primary Examiner* — Michael I Ezewoko
(74) *Attorney, Agent, or Firm* — Shumaker & Sieffert, P.A.

(57) ABSTRACT

In general, techniques are described by which to enable code generation for clinical research systems. A computing device comprising a memory and a processor may implement the techniques. The memory may store a code generator. The processor may execute the code generator. The code generator may determine data collected in support of a clinical research study, and obtain a first mapping between the collected data and an intermediate concept that uniformly classifies the collected data. The code generator may also obtain a second mapping between the intermediate concept and a standard model that conforms to a regulatory standard. The code generator may further generate, based on the first mapping and the second mapping, transformational data that defines a transformation between the data collected in support of the clinical research study and data that conforms to the standard model, and output the transformational data.

25 Claims, 11 Drawing Sheets

CODE GENERATOR FOR CLINICAL RESEARCH STUDY SYSTEMS

TECHNICAL FIELD

This disclosure generally relates to systems for managing clinical studies.

BACKGROUND

Data standards are often developed and used as a uniform communicative structure for the transfer of data from one entity to another entity. These data structures may be used by a receiving entity so that data can be processed in a known format for efficiency and validation during processing. Regulatory agencies are becoming advocates of data standards for submission, analysis, and approval of pharmaceutical products. However, implementation of data standards is often burdensome and expensive for industry. Moreover, as a data standard is changed or updated, the implementation of the standard may need to be changed or updated, which may require significant programming efforts and further expense.

In addition, transformation of data from various settings (e.g., clinical, lab, etc.) to formats that conform to regulatory data standards may involve complex transformation programs that have to be validated (often through double programming of the same transformation) to ensure data consistency prior to submission with regulatory agencies. These programs may consume significant time and resources (both in terms of human programming resources and costs associated therewith) to ensure regulatory compliance of the resulting standard data models submitted to regulatory agencies.

SUMMARY

In general, the disclosure describes techniques for digitizing a framework for clinical development. In some examples, a system as described herein defines a data model that specifies a data standard representative of requirements for regulatory-compliant exchange of data between entities and stores metadata for the data model in a metadata repository (MDR). The data model includes one or more client business objects representing aspects of a well-structured pharmaceutical clinical research study. A clinical research study (also referred to herein as a "study") is, for example, a clinical research project whose objectives are to test or confirm hypotheses concerning the utility, impact, pharmacological, physiological, and/or psychological effects of a particular treatment, procedure, drug, device, biologic, food product, cosmetic, care plan, or subject characteristic. Each study as a whole specifies one or more study events, (referred to herein as "study events" or "events"), where each study event of the one or more study events specifies one or more study activities (also referred to herein as "study activities" or "activities") to be planned for the study event.

In addition to the events and activities mentioned above, the data model further includes additional study data elements (referred to herein as "study elements", "protocol elements" or "elements") each of which is represented as a dynamically configured property within the MDR. These properties are collected into one or more dynamically configured property groups, also specified within the MDR, with each property group representing a section of the study (referred to herein as "study section" or "section') whose elements are cohesively related. Section examples include Planned Intervention, Eligibility Criteria and Study Model Elements among others. These properties may be aggregated into standardized data sets for purposes of regulatory submission, or used to inform other aspects of study design (e.g., the authoring of a study protocol document that specifies the study in narrative form, submission of which is also a regulatory requirement).

The system uses the metadata stored in the MDR to generate a study template for planning a clinical research study. A user interface obtains input from a user to parameterize the study template and store the parameterized template in a database. The system further generates, based on the template, a sequence of one or more study events specifying one or more study activities to be executed for the study event. In some examples, the system may further generate, based on the template, one or more study sections each of which is composed of one or more study elements. In some examples, the system may further generate, based on the template, at least one study objective and at least one study estimand or endpoint (referred to herein as "endpoint") that may be used to facilitate generation of key activities and events within a schedule of study activities.

Rather than manually program transformations to perform translation (or, in other words, transformation) of clinical study data to conform to a regulatory data standards in compliance with regulatory bodies, the system may automatically generate transformations using the definition of study activities, which dictates collection of data, and the MDR, which defines the standardized formats requires by regulatory bodies. The system may automate the transformation as a series of mappings, a first mapping from the definition of the study activity to intermediate concepts and a second mapping from the intermediate concepts to a standards data model that conforms to the regulatory data standards.

The system may employ the intermediate concepts as a uniform semantic layer, allowing multiple variables used for denoting collected data to be mapped to the same concept. This semantic layer may then define a straightforward mapping between concepts and the standard data model that conforms to regulatory data standards. In this way, multiple different variables can be mapped to the standards data model but only a single transformation between each concept and standard data model need to be defined (which is reused by populating a field with each different variable name).

As a result of avoiding manual programming (and possible independent reprogramming) of transformation, the system may improve data transformation, avoid human error, reduce time spent developing transformations, and the like. The increased accuracy and speed of developing transformations may promote more efficient submissions while still remaining flexible to different data collection practices in different settings (e.g., clinics, labs, etc.).

As such, various aspects of the techniques described in this disclosure may result in more efficient operation of the system itself (in terms of avoiding errors that require extensive troubleshooting and consume computing resources, such as processing cycles, memory, bus bandwidth, etc. along with associated power) while also promoting better data consistency that conforms to strict regulatory data standards and facilitating more efficient study design and execution. Improving study times may result in the development of different therapies, medical devices, pharmaceuticals, etc. that clears regulatory bodies in less time and for less cost, which may promote more rapid development of therapies, medical devices, pharmaceuticals, etc. that may improve patient outcomes.

In one example, various aspects of the techniques are directed to a method comprising: determining, by a code generator executed by processing circuitry, data collected in support of a clinical research study; obtaining, by the code generator, a first mapping between the data collected in support of the clinical research study and an intermediate concept that uniformly classifies the data collected in support of the clinical research study; obtaining, by the code generator, a second mapping between the intermediate concept and a standard model that conforms to a regulatory standard; generating, by the code generator and based on the first mapping and the second mapping, transformational data that defines a transformation between the data collected in support of the clinical research study and data that conforms to the standard model; and outputting, by the code generator, the transformational data.

In another example, various aspects of the techniques are directed to a computing system comprising: a memory configured to store a code generator; and one or more processors configured to execute the code generator, the code generator configured to: determine data collected in support of a clinical research study; obtain a first mapping between the data collected in support of the clinical study and an intermediate concept that uniformly classifies the data collected in support of the clinical research study; obtain a second mapping between the intermediate concept and a standard model that conforms to a regulatory standard; generate, based on the first mapping and the second mapping, transformational data that defines a transformation between the data collected in support of the clinical research study and data that conforms to the standard model; and output the transformational data.

In another example, various aspects of the techniques are directed to a non-transitory computer-readable storage medium having instructions stored thereon that, when executed, cause one or more processors to: determine data collected in support of a clinical research study; obtain a first mapping between the data collected in support of the clinical study and an intermediate concept that uniformly classifies the data collected in support of the clinical research study; obtain a second mapping between the intermediate concept and a standard model that conforms to a regulatory standard; generate, based on the first mapping and the second mapping, transformational data that defines a transformation between the data collected in support of the clinical research study and data that conforms to the standard model; and output the transformational data.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

Like reference characters refer to like elements throughout the figures and description.

DETAILED DESCRIPTION

Figure 1:
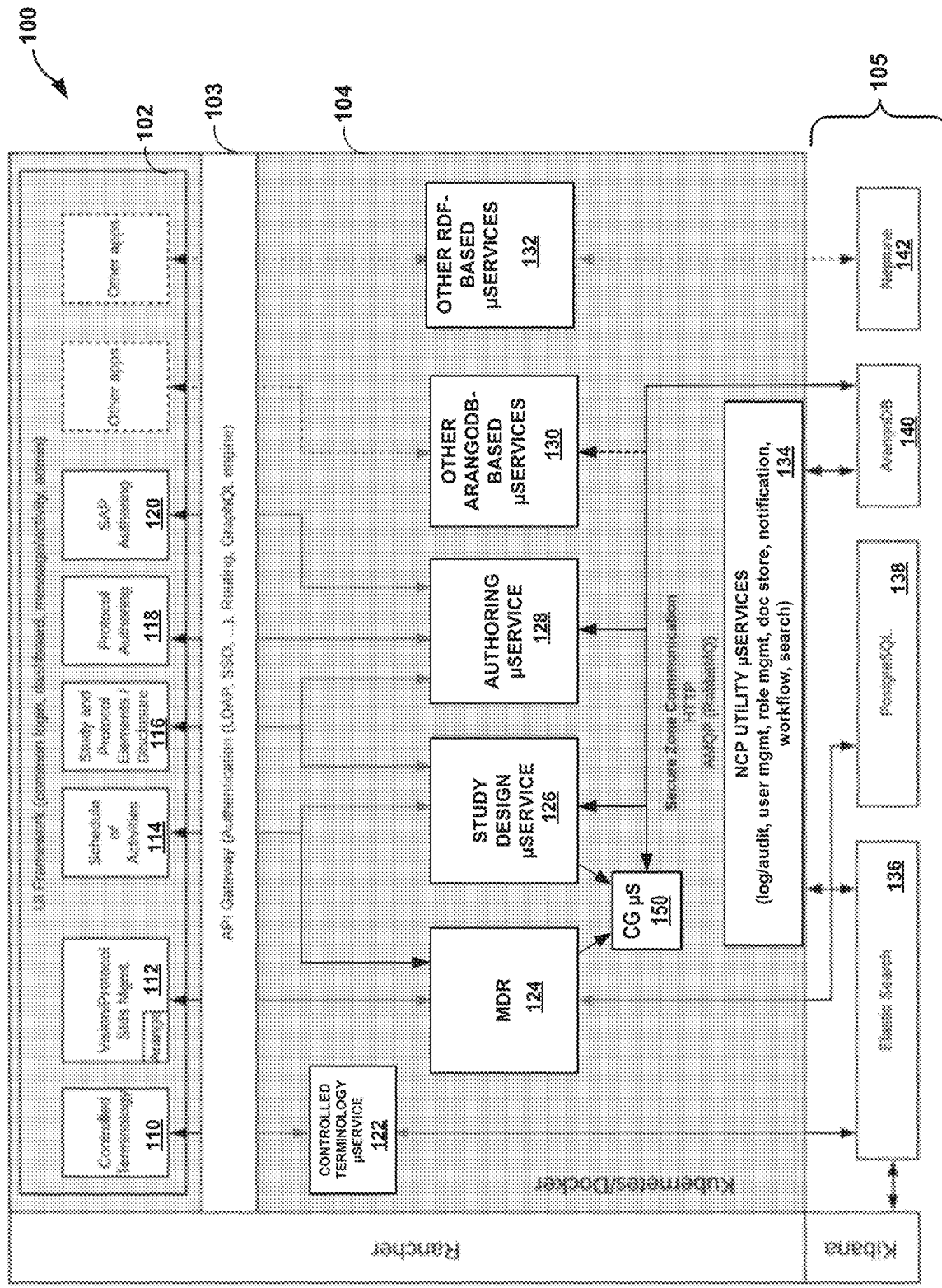
FIG. 1 is a block diagram illustrating an example system for generating a digitized framework for clinical development in accordance with the techniques of the disclosure.

FIG. 1 is a block diagram illustrating example system 100 for generating a digitized framework for clinical development in accordance with the techniques of the disclosure. System 100 includes UI framework 102, microservice platform 104, and database 105. System 100 further includes API gateway 103 which interfaces between UI framework 102 and microservice platform 104.

System 100 provides a clinical lifecycle management application suite and provides a technology platform that supports multiple means of integration and collaboration. System 100 is architected according to various core principles, such as modularity and flexibility, scalability resiliency and security, and openness and pluggability.

System 100 uses a microservice-based architecture, which provides a flexible way by which of building out incremental functionality, with each microservice deployed within the platform controlling that microservice's own data and collaborating with other microservices and UI based applications via one or more APIs, with API gateway 103 serving as both a security layer and an internal routing mechanism for such APIs. Microservices also enable multiple programming languages to be used within the same deployment platform. In some examples, system 100 uses a mix of Java and node.js languages to develop fit-for-purpose components.

UI framework 102 provides a framework for various applications to provide information to a user. Typically, an application of UI framework 102 operates in conjunction with a corresponding microservice of microservice platform 104. In the example of FIG. 1, UI framework 102 includes controlled terminology application 110, which operates with controlled terminology microservice 122 of microservice platform 104 to support the ingestion of updates (e.g., quarterly updates) of controlled terminology from CDISC and NCI.

UI framework 102 further includes protocol standards management application (also known as Vision) 112, which operates with MDR 124 to provide clinical standards management. Schedule of study activities application 114, Study and Protocol Elements/disclosure application 116, protocol authoring application 118, and statistical analysis plan (SAP) authoring application 120 operate in conjunction with study design microservice 126 and authoring microservice 128 to facilitate the digitization and automation of clinical research studies in accordance with various aspect of the techniques described herein.

Each microservice 122, 124, 126, 128, 130, and 132 communicates within the platform and to UI framework 102 through APIs. System 100 may represent an API-first platform that employs a combination of GraphQL based APIs as well as (REpresentational State Transform) REST-based APIs to support intercommunication both within the server side of the platform as well as communication via network-based UI applications and via direct API calls.

With respect to UI-based applications 110, 112, 114, 116, 118, 120, system 100 implements a common UI framework 102 that many if not all applications consume. UI framework 102 provides a seamless cross-application navigation interface such that a user of system 100 is not aware that the user is using multiple applications. Instead, the user simply navigates from capability to capability as he or she goes about their daily work. Lastly, system 100 supports multiple data persistence platforms and enables the easy addition of support for additional data platforms in the future.

In some examples, from a scalability, resiliency and security standpoint, system 100 uses a combination of Docker and Kubernetes as a deployment backbone. Docker enables the packaging up of stateless applications or components, such as microservices and UI-based applications, in a reusable fashion. Kubernetes then combines its capabilities with Docker to manage Docker instances within a runtime environment, automatically scaling those capabilities, potentially ensuring that the instances stay up and running as well as managing restarts when needed, and otherwise providing effective administrative capability over the runtime of the platform.

An administrator may manage system 100 through Rancher, which is an example of an administrative user interface to manage the Kubernetes environment. System 100 also provides access to Elastic Search 136 from a log and audit standpoint through a Kibana UI front end, which is part of the ELK (Elasticsearch, LogStash, Kibana) suite. Although described with respect to a particular front end user interface (UI), e.g., Kibana UI, for accessing ELK databases, and a particular database, system 100 may utilize different front end UIs and databases as is commonly understood in the art.

System 100 may provide a secure and flexible perimeter around back-end microservices that are managing data (with regard to the study design and planning but not clinical or other sensitive data) via a purpose-built API Gateway 103. System 100 may conform to industry-hardened components within this implementation to provide core endpoint security, to potentially provide the flexibility to plug in multiple authentication approaches such as (Lightweight Directory Access Protocol (LDAP)) and various types of Single Sign-On (SSO) and to support federation of GraphQL APIs. API Gateway 103 may also provide other baseline capabilities, such as health check support, for the various components in the platform and a means for components to register as the components become accessible through remote execution.

System 100 is possibly architected to be open and pluggable via the use of APIs that facilitate loosely coupled integration. These APIs support both technical integrations around the utility capabilities of the platform as well as functional integrations that support the clinical lifecycle. Above and beyond this loosely coupled API support, system 100 supports deep integration through a well-defined set of internal microservice APIs 122, 124, 126, 130, 132 and a reusable UI Framework 102. These interfaces enable partners and customers to develop natively-deployed microservices and UI apps that execute seamlessly alongside capabilities provided by system 100.

In some examples, the runtime of system 100 is based on Docker. Docker is a container virtualization environment that enables components based on Java, node.js and other programming languages to share a set of pooled runtime instances. These images are then configured to be deployed within cloud platforms or into properly-configured on-premises (so-called "on-prem") environments in a reusable and scalable manner. Kubernetes supports platform scalability and resiliency by providing a management backbone for these Docker instances. Once configured, Kubernetes establishes various clusters of runtime containers and establishes affinity for various components that one is deploying into those containers. Kubernetes may then manage those capabilities to ensure that the platform remains available for execution of the containers. Kubernetes also provides a communication backbone in the form of a private IP network.

The architecture of system 100 builds upon common data stores by provisioning data stores of various types. In some examples, system 100 leverages relational data stores in the form of PostgreSQL 138, document type NoSQL data stores in the form of Elastic Search 136, and combination document/graph type data stores in the form of ArangoDB 140. System 100 may also integrate with other data stores, such as RDF triple stores. Rancher provides a UI for managing Kubernetes instances, and Kibana provides effective log and audit retrieval and analysis capabilities on top of Elasticsearch 126.

System 100 includes a security layer between the server side of the platform and the outside world, e.g., the Internet or other public networks. System 100 creates a secure "green zone" within Kubernetes taking advantage of the private IP network that Kubernetes provides. System 100 also supports internal message queue-based communication through Advanced Message Queueing Protocol (AMQP) provided by a RabbitMQ instance. All of this is secured behind a purpose-built application programming interface (API) gateway 103. API gateway 103 provides a secure perimeter for API exposure to the Internet, both to applications of system 100 as well as for direct integration from other partner platforms or customer direct usage.

API gateway 103 may also enable pluggable authentication through various authentication strategies, including, for example, lightweight directory access protocol (LDAP), header based single sign-on (SSO), security assertion markup language (SAML) based SSO, or open identification (OpenID). Other authentication strategies may also be enabled via this pluggable authentication framework. API gateway 103 integrates a GraphQL engine that allows microservices 122, 124, 126, 128, 130, 132 to provision their portion of the data graph into a federated GraphQL API. This GraphQL API aggregates data content across all the various microservices supporting system capabilities. This provides increased client-side ease of use and efficient access to content provided by system 100.

System 100 uses both a common UI framework 102 and a back-end set of utility microservices 134. UI framework 102 provides all applications with common login, common user session management and seamless cross-application navigation, with applications registering into the framework such that they are able to communicate and navigate with each other. UI framework 102 also provides various shared end user and administrative UI elements including a library of common widgets and other components that are available for application development. In the back-end, system 100 provides a suite of utility microservices that in essence provide the shared technical capabilities needed in order to build out an enterprise-class application platform suite. Capabilities such as dynamic properties, comments, change requests, logging, audit, user management, role and permissions management (i.e., access control), document store, reporting, notifications through multiple channels, integrated workflow and integrated cross-application search are part of utility microservice suite 134.

System 100 enables data standards management by an underlying metadata repository (MDR) 124 that is embedded within system 100. MDR 124 is an ISO 11179-based MDR that support the provisioning of configurable content. In some examples, MDR 124 is a regulatory database based on a governance process that defines a protocol model for storing metadata. This metadata is managed to ensure that version control is maintained as the platform and its capabilities mature over time. Robust workflow and governance capabilities of the system 100 apply both as new clinical data standards (CDISC and others) are specified and provisioned and as new program, protocol and study standards are defined and refined.

In some examples, MDR 124 is prepopulated with clinical data acquisition standards harmonization (CDASH) to study data tabulation model (SD™) transformation rules. As organizations continue to build out more efficient clinical lifecycle execution, MDR 124 may incorporate additional rule-based transformations (including internal standards transformations and transformations from SDTM to analysis data model—ADaM). MDR 124 may express rules in narrative or executable form (for example statistical analysis system—SAS—program fragments). Additional models and transformation rules between models may be incorporated as required to support clinical trial modeling, definition and execution.

MDR 124 is an ISO 11179-based MDR that support the provisioning of configurable content. This metadata is managed to ensure that version control is maintained as the platform and its capabilities mature over time. Robust change request, workflow and governance capabilities of the system 100 apply both as new clinical data standards (CDISC and others) come on board and as new program, protocol and study standards are defined and refined.

MDR 124 is exposed to data standards curators and other standards management personnel through Critical Data Standards Management application 112 (also known as Vision). Vision provides a very flexible yet end user centric view over MDR content. MDR 124 includes technical components and Vision allows the presentation of MDR content in a context that is meaningful to managers of that content. Controlled terminology microservice 122 and application 110 augment MDR 124 by supporting the ingestion of updates of controlled terminology from CDISC and NC. Thus, MDR 124 may provide a flexible application that supports effective identification of the intersection between new terminology and existing internal terminology defined by clinical organizations and helps customer organizations manage the impact of adopting newly defined terminology on a case-by-case basis. API Gateway 103 in turn exposes data standards APIs that allow system 100 to support downstream data platform provisioning with other customer or vendor platforms.

In addition to supporting direct content access externally via GraphQL API calls, the platform also provides reporting microservice 134 which exposes platform content via configured REST APIs. Each configured API is exposed via API gateway 103 and is associated with an internal GraphQL query that retrieves content of interest for the report. Query results are then provided to a configurable formatting engine that is part of microservice 134. The formatting engine collects, organizes, and transforms the contents of query results into the desired output in the form of java script object notation (JSON), extensible markup language (XML), Microsoft Excel spreadsheet (XLSX), comma separated values (CSV) and/or portable document format (PDF) as required by the expected user of the configured API. In one example, reporting microservice 134 maps an inbound REST API request to a specific service configuration that defines how to fetch the data needed for the response, how to traverse that data, and how to prepare the response. The incoming request mapping is routed based on the parameterized resource path of the incoming resource request.

Once mapped, the service configuration informs which GraphQL query to run against the system's federated GraphQL interface. This query may be tuned to specify the data attributes needed to satisfy the request. The GraphQL response is a JSON object that is further processed by reporting microservice 134. The JSON object is traversed based on the service configuration and is defined in terms of data views, each of which consists of data selectors and (further recursive) data views. During traversal, the recursion algorithm sends events to a formatter when a view starts, a data selector delivers data, or when a view ends. Formatters are agnostic to the actual request, data source or traversal. They prepare a data export based on the events such formatters receive. Each formatter is specialized for a specific export format based on the media type of the original request. Reporting microservice 134 may support response formats for Excel, CSV, JSON, XML, and PDF media types. In another example, the reporting microservice configuration supports the application of XSLT transformations for XML based media types.

Study design microservice 126 sits at the core of the clinical lifecycle management suite provided by system 100. Study design microservice 126 provides a fully digital clinical research study representation ranging from study initialization parameters such as therapeutic area and indication, study-specific objectives and endpoints, all the way through to a full fidelity schedule of study activities with study events and study activity items that are to be executed for those study events. Both industry-wide and corporate clinical standards may be automatically sourced from MDR 124 in support of study design microservice 126.

Study and protocol elements application 116 manages the wide range of elements organized into pages and sections that are necessary to populate and define a fully specified study. A key aspect of this application is the objective and endpoint editor. This editor exposes predefined templates managed within the MDR 124, providing a study designer with an intuitive and easy to use UI when defining primary, secondary, or exploratory objectives and endpoints for the study under development. These objectives and endpoints establish a basis for the scientific hypotheses to be experimentally assessed by the study. Study and protocol elements populated via this application are persisted in study design microservice 126, where the elements become available for downstream systems use including automated disclosure capabilities to relevant authorities.

Schedule of study activities application 114 provides a fully digitized clinical research study schedule development environment that leverages objectives and endpoints that have been previously specified to provide automated suggestions for schedule study events as well as study activities to be executed during those study events. Schedule of study activities application 114 directly consumes industry and corporate data standards automatically from MDR 124 such that once the user has completed schedule definition, a full fidelity schedule is then stored in study design microservice 126, synchronized back to MDR 124 for impact analysis purposes and ultimately enabled for export (via file extract, API invocation or other means) to downstream customer or vendor platforms. In other examples, the full fidelity schedule may be stored in one or more special purpose microservices for impact analysis and export purposes.

System 100 provides an additional protocol standards management capability in the area of data standards via MDR 124. A clinical data standards management application facilitates defining reusable objective and endpoint templates along with other data elements in support of clinical research study lifecycle applications.

Authoring microservice 128 and application suite 118 provide protocol authoring capabilities. In one example, this suite supports a fully digitized implementation of a protocol model of a clinical research study along with other templatized content. Authoring microservice 128 and application suite are natively integrated with study design microservice 126 and MDR 124. Authoring microservice 128 is fully templatized so that one may apply additional templates to support customer-specific protocol formats, and support alternative documents such as Statistical Analysis Plan (SAP) authoring 118.

Microservice developers may pick from a wide range of programming languages and data persistence platforms. Specifically, system 100 may incorporate both portfolio and program level applications such as portfolio management, indication analysis, target product profile (TPP), clinical development plan (CDP), and protocol synopsis as well as study execution centric applications and support of topics such as feasibility and recruitment, risk management, and supply management. These additional applications are examples only and are not intended to limit the scope of system 100.

System 100 uses database 105 to store, manage, and retrieve content for clinical development. Database 105 may take various forms, such as a relational database, a document-based database, and/or a graph-based database. In the example of FIG. 1, database 105 is implemented with Elastic Search 136, PostgreSQL 138, ArangoDB 140 and/or Neptune (an example of an RDF Triple Store database) 142. In some examples, database 105 implements GraphQL queries and mutations to manage data. For example, study design microservice 126 implements GraphQL APIs that invoke database 105 as an efficient and flexible way to retrieve clinical development content.

Microservices 122, 124, 126, 128, 130, 132, and 134 are "GraphQL first" in nature. Microservices 122, 124, 126, 128, 130, 132, and 134 expose core Create/Read/Update/Delete (CRUD) actions on their business objects via GraphQL queries and mutations. GraphQL, originally developed by Facebook, Inc. (now Meta, Inc.) as part of its microservice-based platform architecture, provides two possible features that make GraphQL well-suited for such development: federation and field (attribute) selectivity.

GraphQL supports the concept of API federation, where each microservice contributes its business object declarations to an all-encompassing graph spanning the entire set of business objects deployed into the platform. This federated view is exposed by a single GraphQL API endpoint. As each new microservice 122-134 is deployed into the platform, the microservice augments this object graph with the new objects for which it has responsibility. A GraphQL API consumer can in turn initiate a single API query that spans as much of the graph as is needed, with server-side infrastructure efficiently merging the content to support the API request.

Field selectivity in GraphQL is a natural complement to business object federation, as GraphQL allows API consumers to precisely identify which object fields (attributes) are to be returned in query results. This eliminates the potential concern of very large datasets being returned to the client in response to a broad query invocation, while at the same time eliminating the need to implement multiple purpose-specific APIs supporting various combinations of object content to suit the needs of the client. Because GraphQL supports field selectivity, it is easy to modify a full query to database 105 by removing various elements to produce a result that aligns with desired view of the template graph aligned for ease of use to the customer. The result may in turn be transformed from JSON into other representations (e.g., HTML) via reporting microservice 134, UI framework 102, or other means.

System 100 may operate to generate dynamically configured applications composed of pages and sections within pages. Contextual properties such as ordinality, read-only, multivalued and required are used by the UI to present the property correctly within the page section in question. Different property subtypes require specialized context properties; for instance, ordered literal types such as integer, decimal, date and timestamp include optional properties such as lower and upper bounds and Boolean flags that indicate inclusive or exclusive bounds settings. Dynamically retrieved types such as user specific attributes such as permission name (derived from system configuration used to specify access control microservice 134 behavior) and associated resource type, and include optional properties such as whether the current user is to be included in the dynamically retrieved results for the property.

Enumerated properties may be specified by value lists within MDR 124, or those value lists may be dynamically retrieved from sources external to MDR 124 (e.g., a list of platform users with a specified role may be retrieved from the system's User microservice in concert with the access control microservice, a list of valid protocol numbers may be retrieved from an external clinical trial management system (CTMS)). Compound property types (which compose two or more elemental property types) may also be specified within the system. One example of a compound property type is a representation of a Study Event composed of a period type (enumerated value list composed of values such as Day, Week, Month) and integer. The study event property type may support automatic generation of study events via endpoint template parameterization.

Conditional property specifications, where default contextual properties are modified given a specific set of conditions, are also supported. For example, a property A may become editable only when a property B contains a specific value, or when property B is populated with any value. Conditions may span multiple specified values for a designated property (e.g., property C must be set to one of values x, y, or z for the condition to be in effect) and may span multiple designated properties (e.g., the conditional rules for properties D, E and F must all be met for the condition to be in effect).

In general, system 100 enables the digitization of a framework for clinical development. For example, study design microservice 126 uses metadata stored in MDR 124 to generate a study template for performing a clinical research study. UI framework 102 obtains input from a user to parameterize the study template and store the parameterized template in database 105. User input includes an Effective Date parameter which is defaulted to the current date and may be modified by the user. The Effective Date value is used to automatically retrieve the correct version of study and protocol standards from which the study template will be generated.

As such, different versions of the study template may be associated with a corresponding Effective Date parameter and thereby facilitate retrieval of a correct version of the study template representative of the governance process identified by the Effective Date parameter. The correct version is selected by identifying the version with a specified date most recently prior to the Effective Date specified for the study. For example, if three versions of the study template exist, with version 1 specified date set to Jan. 31, 2018; version 2 set to Oct. 15, 2019; and version 3 set to Dec. 31, 2020, then Study A with an effective date of Jul. 15, 2019 would be assigned version 1, Study B with an effective date of Jan. 15, 2020 would be assigned version 2, and Study C with an effective date of Apr. 30, 2021 would be assigned version 3. The ability to specify an Effective Date may be useful for long-running Clinical Development Programs (e.g., for an Oncology Therapeutic Domain) where Studies within a Program span years and for which a consistent set of standards must be applied.

Study design microservice 126 generates, based on the template and potentially combined with user input, a sequence of one or more study events specifying one or more study activities to be executed for the study event and study elements associated with the clinical research study. As described herein, a "study event" refers to a checkpoint during a clinical research study at which specific study activities are performed. The study event specifies one or more study activities to be executed for the corresponding study event. Each study activity may be, e.g., a clinical assessment or procedure to be performed on a subject, a data element to be measured from the subject, an assemblage of already existing data about the subject, or collection of non-treatment related data (e.g., healthcare utilization) from the subject. The detailed specification of a study activity is based on data collection standards (e.g., CDASH) as governed within MDR 124, thus linking these collection standards (and by extension tabulation, analysis and other data standards via transformation rules also governed in MDR 124) to the study template and protocol standards also specified within that template. For example, a study event for a study objective may occur on a periodic basis (e.g., daily, weekly, or monthly) and specify that a study activity to be performed, for example, that a subject's blood pressure and heart rate be monitored. In this way, a clinical research study may be quantized into a sequence of such study events and study activities, and thereby objectively defined and measured.

Study elements are planning related data elements that a regulatory authority may require the collection of during the clinical research study. Further, the regulatory authority may require the submission of such study elements to the regulatory authority as part of reporting requirements of the clinical research study. System 100 enables the collection of study element data via configuration of properties and property groups specified as part of the study template and managed within MDR 124. System 100 manages these configured elements as configured sections within study design microservice 126 and directly persisted via dynamic property microservice, one of utility microservices 134. Dynamic property microservice 134 may accept study elements by study design microservice 126 through advanced message queuing protocol (AMQP) messages informing dynamic property microservice 134 of the study element sections specified in the template used for the study. Use of asynchronous messaging in this manner may preserve loose coupling between microservices.

In some examples, the specific types of study elements are mandated by the regulatory authority (e.g., as CDISC submission data sets). Examples of study elements include data related to pharmaceutical administration, sponsor information, study planning, or study extensions. Study elements related to pharmaceutical administration may include a dose formulation of the pharmaceutical studied in the clinical research study, a route of administration, a dose per administration, a dose regimen, dose units, or dosing frequency. Study elements related to sponsor information may include a responsible party, a sponsor status, a sponsor name, sponsor contact information, a sponsor legal address, a sponsor telephone number, or a sponsor email address. Study elements related to study planning may include a planned number of subjects, a planned treatment duration, a stable disease minimum duration, a confirmed response minimum duration, a planned trial duration, or study stop rules. Study elements related to study extension may include an extension trial indicator, a substudy planned indicator, or substudy details.

In some examples, study design microservice 126 may further generate, based on the template, at least one study objective and at least one study endpoint that may be used to facilitate generation of key activities and events within a schedule of study activities. A study objective specifies a hypothesis for the clinical research study. A study endpoint specifies a means by which the hypothesis is evaluated (e.g., a lab test, physiological measurement, or other data point). Each study event may be linked to a study objective and an associated study endpoint of the study objective. For example, a study endpoint is defined within the scope of a study objective, and the study endpoint is the means by which one establishes connectivity to a corresponding study activity for a study event. In other words, the study endpoint allows for the definition of one or more relevant study activities to be executed in associated study events. In some examples the study endpoint is connected to one or more study activities via introduction of a Biomedical Concept resource type within MDR 124.

By defining a hypothesis through a study objective and a process for testing the hypothesis with a corresponding study endpoint, system 100 may generate a sequence of study events and study activities to be performed for each study event such that system 100 may objectively define the clinical research study as well as a procedure for implementing and carrying out the clinical research study. Various applications executing within microservice platform 104 may generate a schedule of study activities and study events to implement the study, generate reporting information and documentation, and/or determine a cost estimate for each study activity of the study.

Study design microservice 126 may also enable the specification of repeated activities during a single study event. Such a specification is called a timepoint schedule. Consider the scenario where a study event X includes drug administration (Exposure) followed by repeated measurements of Vital Signs, e.g., 10 min, 20 min, and 30 min after drug exposure. In this scenario, the Exposure study activity is marked once on the main schedule for study event X and a timepoint schedule with three timepoints is created for study event X. The Vital Signs study activity is then scheduled for observation at each of the timepoints.

To support the digitized framework for clinical development described herein, MDR 124 extends the data model set forth in ISO 11179. For example, MDR 124 implements a data model that specifies a data standard representative of requirements for regulatory-compliant exchange of data between entities and stores metadata for the data model. As described herein, the data model includes one or more client business objects representing aspects of a well-structured pharmaceutical clinical research study. As described herein, a clinical research study is, for example, a research project whose objectives are to test or confirm hypotheses concerning the utility, impact, pharmacological, physiological, and/or psychological effects of a particular treatment, procedure, drug, device, biologic, food product, cosmetic, care plan, or subject characteristic.

MDR 124 extends each client business object to represent a clinical research study or associated study element, whereas each clinical research study in turn specifies one or more study events. Each event specifies one or more study activities to be executed for the corresponding study event. MDR 124 further extends the data model of ISO 11179 to include one or more properties for each of the client business objects that organize the client business objects into one or more property groups. These properties and property groups are used to represent both cohesive collections of study elements (i.e., sections) and configurable elements of objective and endpoint templates.

The extended data model implemented by MDR 124 enables the digitization of clinical research studies as described herein by templatizing various data for clinical research study such that clinical research studies may be standardized and preformatted, and specific instances of clinical research studies may be rapidly designed. As such, system 100 may enable the digitization of clinical research studies, clinical research study management, and clinical research study reporting requirements so as to potentially obviate the performance of clinical research study management by hand. Therefore, system 100 may improve efficiency and data quality, reduce submission cycle times, reduce the cumbersome administrative overhead of clinical research study management by hand, as well as reduce the potential for error or omission in critical recordkeeping. Planning and design data for clinical research studies are stored in database 105.

As discussed above, study design microservice 126 generates, based on the template and potentially combined with user input, a sequence of one or more study events specifying one or more study activities to be executed for the study event and study elements associated with the clinical research study. As described herein, a "study event" refers to a checkpoint during a clinical research study at which specific study activities are performed. The study event specifies one or more study activities to be executed for the corresponding study event. Each study activity may be, e.g., a clinical assessment or procedure to be performed on a subject, a data element to be measured from the subject, an assemblage of already existing data about the subject, or collection of non-treatment related data (e.g., healthcare utilization) from the subject.

Study design microservice 126 may define data collected for each of the study activities as a variable. Data specified for these variables may then need to be transformed into the format of MDR 124, which as noted above conforms to various regulatory data standards. In practice, a data transformation specialist programs (or, in other words, codes) the transformations using a programming language, where the resulting code transforms the data from the collected format to a format that conforms with the regulatory data standards. This transformation is necessary to allow the regulatory body to more quickly understand and process the data to assess the success of the study.

To ensure proper transformation, typically each code defining the transformation is programmed twice by independent data transformation specialists. The results of each transformation are then compared to identify any differences in the transformations. Once all differences have been removed between the comparable transformation code, there is a high probability that the data resulting from application of the transformation code adheres to the regulatory data standard, and thus is ready to be provided to the regulatory body in support of clinical study.

As such, transformation of data from various settings (e.g., clinical, lab, etc.) to formats that conform to regulatory data standards may involve complex transformation programs that have to be validated (often through double programming of the same transformation) to ensure data consistency prior to submission with regulatory agencies. These programs may consume significant time and resources (both in terms of human programming resources and costs associated therewith) to ensure regulatory compliance of the resulting standard data models submitted to regulatory agencies.

In accordance with various aspects of the techniques described in this disclosure, system 100 may automatically generate transformations rather than manually program transformations to perform translation (or, in other words, transformation) of clinical study data to conform to a regulatory data standards in compliance with regulatory bodies. System 100 may automatically generate the transformation using the definition of study activities (e.g., in the schedule of activities), which dictates collection of data, and the MDR, which defines the standardized formats requires by regulatory bodies. System 100 may automate the transformation as a series of mappings, a first mapping from the definition of the study activity to intermediate concepts and a second mapping from the intermediate concepts to a standards data model that conforms to the regulatory data standards.

The system may employ the intermediate concepts as a uniform semantic layer, allowing multiple variables used for denoting collected data to be mapped to the same concept. This semantic layer may then define a straightforward mapping between concepts and the standard data model that conforms to regulatory data standards. In this way, multiple different variables can be mapped to the standards data model but only a single transformation between each concept and standard data model need to be defined (which is reused by populating a field with each different variable name).

As a result of avoiding manual programming (and possible independent reprogramming) of transformation, system 100 may improve data transformation, avoid human error, reduce time spent developing transformations, and the like. The increased accuracy and speed of developing transformation may promote more efficient studies while still remaining flexible to different data collection practices in different settings (e.g., clinics, labs, etc.).

In operation, system 100 includes a code generator (CG) microservice 150 that is executable to perform various aspects of the techniques described in this disclosure. CG microservice 150 may determine data collected in support of a clinical research study. That is, CG microservice 150 may determine, based on the above noted schedule of activities for the study protocol, the data collection elements captured in support of the clinical research trial.

CG microservice 150 may traverse the schedule of activities and identify study events having study activities associated with different types of data, where such data may be denoted using variables (or, in other words, variable names). The data collected in support of the clinical study may conform to clinical data standards that defines how the data is to be captured and mapped to the underlying variable names. CG microservice 150 may further determine a data collection type of the data collected in support of the clinical research study. This data collection type may be referred to herein as a "facet," which provides a uniform classification or, in other words, type of the collected data. For example, a variable for the visit data denoted as "vday" may have an assigned facet of "dayOfCollection."

CG microservice 150 may, based on these variables and facets, obtain a first mapping between the data collected in support of the clinical research study and an intermediate concept that uniformly classifies the data collected in support of the clinical research study. Via UI framework 102, a user may specify these mappings between variable/facet pairs and the intermediate concept. In the example above, a user may map vday (dayOfCollection) to an Observation concept. Additional variables may be mapped to the Observation concept, such as visit month denoted as "vmonth" having a facet of monthOfCollection or visit year denoted as "vyear" having a facet of yearOfCollection.

CG microservice 150 may next obtain a second mapping between the concepts and the standard model (which may also be referred to as a standard data model) that conforms to the regulatory standard. The standard data model may include elements, such as "dtc" which refers to the date of collection and is assigned to the dateOfCollection facet. CG microservice 150 may access MDR 124 to identify these standard data model elements with little to no human oversight. Via UI framework 102, a user may assign the facets to the standard data model elements in order to define potential transformations at a high semantic level using the intermediate concepts to link facets of variables to facets of standard data model elements. CG microservice 150 may then resolve the second mapping using the similar facets that map to the same intermediate concept. As discuss in further detail below, this definitional framework for associating variables by way of associated facets between intermediate concepts that are associated with standard data model elements having the same facet may result in reuse and further automation of the underlying transform.

In any event, CG microservice 150 may generate, based on the first mapping and the second mapping, transformational data that defines a transformation between the data collected in support of the clinical research study and data that conforms to the standard model. CG microservice 150 may generate intermediate data structures to resolve how collected data will be transformed in terms of order with respect to different variables and data sources and/or settings. CG microservice 150 may then generate the transformational data based on the intermediate data structures defining the order of transformation to form cohesive data sets that conform to the regulatory standards, outputting the transformational data for use.

That is, system 100 may not store the actual collected data, but rather symbolically represent the collected data in terms of the variables. Personal health data and any other types of research data may require robust security and compliance with a number of different regulatory standards to ensure patient/test subject privacy. System 100, while potentially adaptable for storing such sensitive data, may not provide sufficient security while also facilitating the study development process by a wide number of different study designers. As such, CG microservice 150 may output the transformation data for execution by users of system 100 at a local repository that stores the collected data and that is subject to more secure environments that complies with the various regulatory standards surrounding sensitive personal health data.

In this way, various aspects of the techniques described in this disclosure may result in more efficient operation of system 100 itself (in terms of avoiding errors that require extensive troubleshooting and consume computing resources, such as processing cycles, memory, bus bandwidth, etc. along with associated power) while also promoting better data consistency that conforms to strict regulatory data standards and facilitating more efficient study design and execution. Improving study times may result in the development of different therapies, medical devices, pharmaceuticals, etc. that clears regulatory bodies in less time and for less cost, which may promote more rapid development of therapies, medical devices, pharmaceuticals, etc. that may improve patient outcomes.

System 100 may be implemented on one or more computing devices that comprise processing circuitry and a memory. In some examples, the processing circuitry is one or more microprocessors, digital signal processors (DSPs), application specific integrated circuits (ASICs), field programmable gate arrays (FPGAs), or any other equivalent integrated or discrete logic circuitry, as well as any combinations of such components. In some examples, the memory is random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Further, this memory may be implanted entirely in hardware, software, or a combination thereof.

Figure 2:
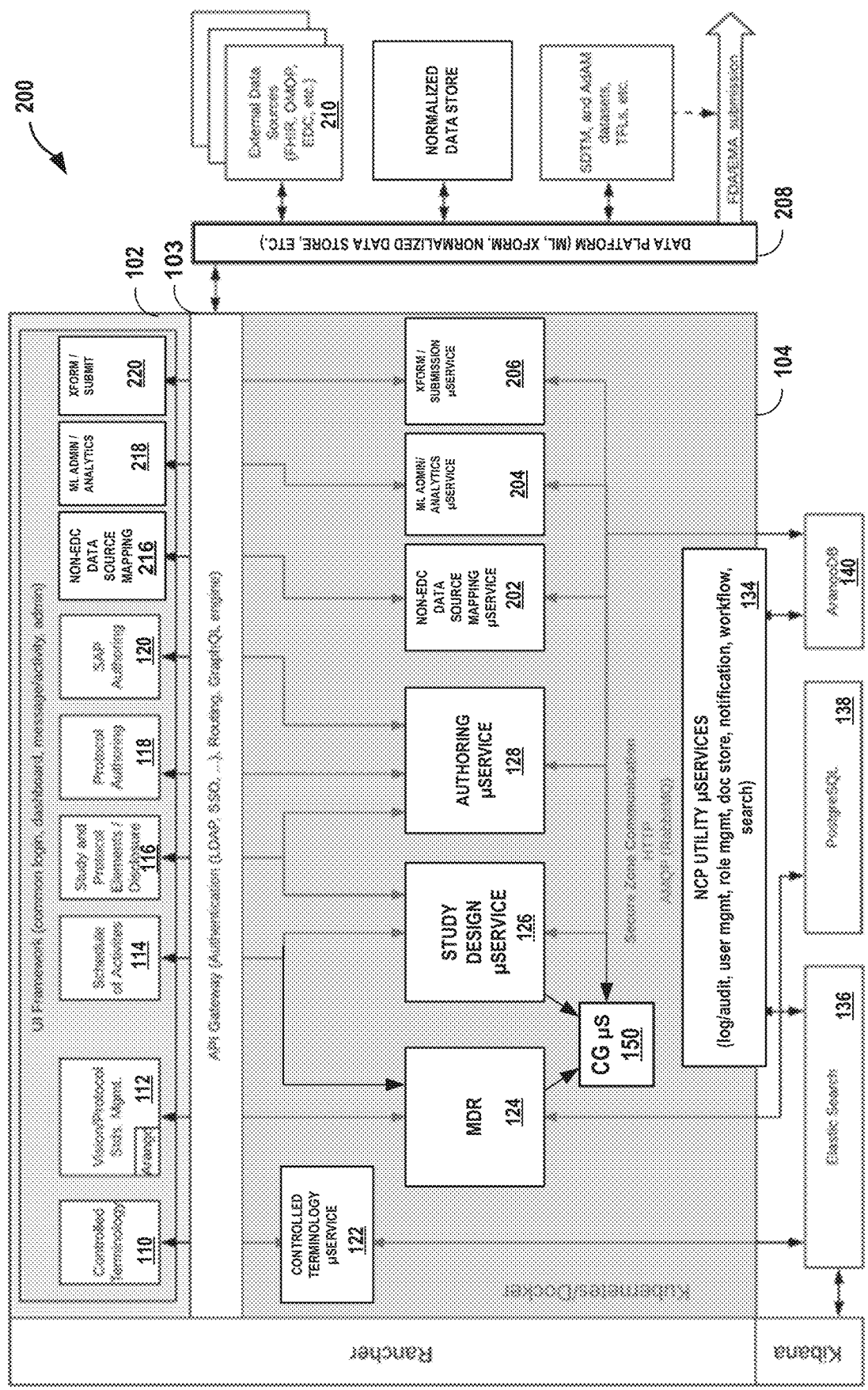
FIG. 2 is a block diagram illustrating another example system for generating a digitized framework for clinical development in accordance with the techniques of the disclosure.

FIG. 2 is a block diagram illustrating example system 200 for generating a digitized framework for clinical development in accordance with the techniques of the disclosure. System 200 may operate in a substantially similar fashion to system 100 of FIG. 1. However, system 200 includes additional application/microservice suites, such as non-EDC data source mapping application 216 and microservice 202, machine learning administration/analytics application 218 and microservice 204, and transform/submit application 220 and microservice 206.

System 200 may operate as an industry-wide integration platform and may support various partner- and customer-specific applications. For example, one partner may choose to specialize in non-EDC data source management, and so system 200 may provide non-EDC data source mapping application 216 and underlying microservice 202 to integrate and consume non-EDC oriented data sources such as the FHIR and OMOP standards. Such an application 216 and microservice 202 consumes content from MDR 124, including additional data standards definitions and mapping rules, to support cross-standard data normalization. Because MDR 124 is an ISO 11179-based implementation, MDR 124 is fully flexible and extensible to support wide ranges of data and other content standards in support of partner and customer goals.

In some examples, system 200 may implement machine learning in aspects of clinical lifecycle development as well as in analysis of legacy protocols and studies in support of future optimization efforts. For example, system 100 may embed machine learning analytics and administrative capabilities application 218 and accompanying machine learning analytics and administrative microservice 202 within microservices platform 104. System 100 may provide a common machine learning framework application and microservice suite in support of customer machine learning initiatives.

In some examples, system 100 implements a submission management application 220 and accompanying microservice 206. Such an application 220 integrates with an external data management platform 208 and/or data warehouse to trigger content extraction, transformation and assembly of submission materials, including CDISC submission data sets directly extracted from Study Design microservice 126 or other functional microservices. This submission management microservice manages submission packages to government authorities such as FDA and EMA, as well as tracks submissions as the submissions are processed.

Figure 3:
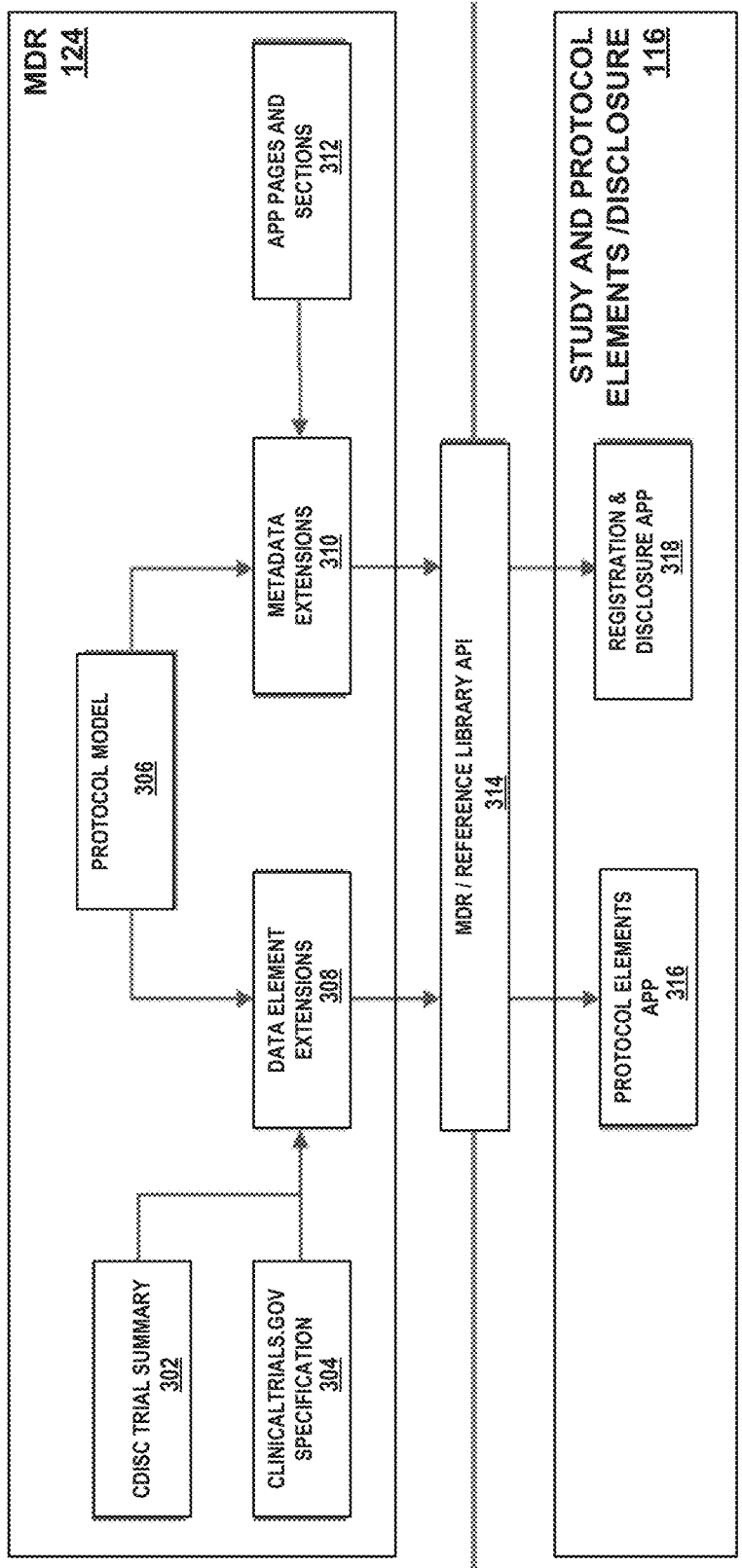
FIG. 3 is a block diagram illustrating interactions between the MDR and the Study and Protocol Elements application of FIG. 1 in accordance with the techniques of the disclosure.

FIG. 3 is a block diagram illustrating interactions between MDR 124 and Study and Protocol Elements application 116 of FIG. 1 in accordance with the techniques of the disclosure. MDR 124 stores and maintains metadata definitions as well as relationships with related metadata types. MDR 124 is an enterprise software system that provides metadata management for an end-to-end data lifecycle including public or private standards or data exchange formats, which can be any established norm or requirement with a formal document that establishes uniform engineering or technical criteria, methods, processes and practices. MDR 124 may implement one or more standards as an authoritative source and governance for creation of metadata as well as automatic inheritance and impact analysis of any proposed changes.

MDR 124 acts as a centralized repository of metadata assets associated with data collection, tabulation, analysis and other representational standards, and a governance platform that supports requirements through configuration, rather than hardcoded behavior requiring custom modification to adapt to changing requirements.

MDR 124 provides and maintains an asset library that stores assets, and presents an interface to index, search and selectively retrieve the assets from the asset library for reuse. In this way, MDR 124 may be implemented to provide, as one example, a centralized organizational metadata repository and governance solution for providing management of standards, semantics, and metadata associated with data collection. In general, MDR 124 allows users to manage metadata assets associated with data standards, where each of the assets is a separate collection of descriptive information about an accepted, standardized data element having semantic context for a given data standard, and where the asset is related in a hierarchical structure within an asset library where each respective asset may have one or more parent or child assets.

As such, entities may use MDR 124 to reuse the collection of information represented by any given asset for implementing different data standards. This may be particularly useful in situations where a standard is built on top of another standard. When this happens, MDR 124 allows users to advantageously create relationships to generic assets. For example, if each asset represents an XML element and each asset attribute represents an XML attribute for that respective XML element, then MDR 124 allows the assets to be used across standards and, for example, for creation of forms for collecting data and for tabulation and reporting of the data, i.e., throughout the entire process.

In some examples, the underlying physical data model used by standards specification and management system 18 may be based on an Object Management Group's (OMG) Reusable Asset Specification, such as Reusable Asset Specification Version 2.2, Object Management Group, November 2005, incorporated herein by reference. Physical content may be organized and constrained by a logical meta-model.

MDR 124 is an ISO/IEC 11179-based MDR. ISO/IEC 11179 standardizes the representation of metadata for an organization in an MDR and documents the standardization and registration of metadata to make data understandable and shareable. An MDR as defined by ISO/IEC 11179 specifies the use of one or more data elements. Each data element specifies a type of data and permits the use of only those values enumerated in a value domain to be used as valid values for the type of data. Further, ISO/IEC 11179 specifies the grouping of related data elements by a high-level concept and an object class, e.g., a data element concept. Additional description of data elements may be found in the ISO/IEC 11179 standard available from the International Organization for Standardization (ISO), the entire content of which is incorporated herein by reference. The baseline logical model provided by standards specification and management system 18 may be based on the ISO/IEC 11179 standard for metadata registries.

CDISC trial summary 302 and ClinicalTrials.gov specification 304 are examples of regulatory authorities, entities, or organizations that specify or receive submissions of clinical study data or clinical research study protocols. For example, a regulatory authority may use submitted data to ensure that proper procedures were followed during a clinical trial or study and/or to approve or reject the introduction of one or more products into the market. Although the techniques are described with respect to a clinical study, the techniques are not so limited and may be applied in other implementations where an agency or organization needs produce a detailed specification for controlling submission of data in accordance with a standard.

MDR 124 allows a user to automatically generate and manage metadata associated with client business objects. In some examples, the metadata may be associated with one or more standards (e.g., associated with one or more data models defined by a data standard). For example, a regulatory authority may define and promulgate one or more standards, such as a data collection standard, a data tabulation standard, or a data submission standard, to which MDR 124 adheres. For a given data submission standard being implemented, MDR 124 tabulates data submitted by users and formats the data according to the data submission standard.

MDR 124 implements one or more data models that represent a data standard for exchanging data. Each data model is a guide or specification that describe standardized data for collection and tabulation. As one example, a model associated with a standard data exchange for clinical research may identify data collection fields needed from a clinical, scientific, and regulatory perspective to enable more efficient and consistent data collection at an investigative site. In one example, a model represents a data standard by defining a schema in accordance with a data description language, such as the extensible markup language (XML), JSON, or other languages not expressly described herein.

In this way, a model may represent a corresponding standard for describing and exchanging data, such as data for clinical studies, in a form that is vendor neutral and platform independent. More specifically, a model may specify a data standard for exchanging data via an XML schema, which uses schema components to define the meaning, usage and relationships of the elements that may be used within a class of XML documents, as well as permissible content, attributes, and values for the elements. In some examples, the data models may include (or potentially specify) assets that define objects for the data model.

MDR 124 operates as a fully integrated asset management system in which data specified in data guides or specifications for data standards are automatically processed and transformed into reusable assets. This metadata can be exported in submission standards such as ODM XML or Define XML, which is an XSD and specification relating business rules, for automatic generation of forms utilized by regulatory authorities.

In some examples, MDR 124 implements the Clinical Data Acquisition Standards Harmonization (CDASH) data collection standard, such as the CDASH v1.1 Standard developed by CDISC.ORG (which is one example of an industry standard) and/or sponsor-specific standards (e.g., pharmaceutical standards, contact research organization (CRO) standards, and/or device manufacturer standards). MDR 124 can be configured to support independent management of multiple sponsor standards in conjunction with shared global standards. This configuration is useful for Contract Research Organizations (CROs) that concurrently execute studies for numerous pharmaceutical, biotech and medical device providers.

In this configuration, the shared global standards (CDISC and/or CRO-defined) are managed at the top (Enterprise) organization of MDR 124. A suborganization is created for each sponsor and clearly named to be easily identifiable as associated with that sponsor. Sponsor-provided and sponsor-specific (i.e., developed by the CRO specifically in support of a sponsor) standards are populated in the suborganization for that sponsor. System users are then assigned specific organizations for which they are allowed access.

For example, User A may be allowed to access Sponsor 1, User B may be allowed to access Sponsor 2, and User C may be allowed to access Sponsors 1, 2 and 3 and the Enterprise (CRO) organizations. When a user logs into system in this configuration, they select an organization for which they are working for the duration of that user session. That user is then allowed to view only those standards contained in the specific organization which they selected, along with the global standards at the Enterprise level if the selected organization is a sponsor organization.

This organizational hierarchy approach may provide two major benefits to a CRO. First, each sponsor is freely able to share/reuse CRO global standards as part of their sponsor-level definitions, where this can greatly improve efficiency for the sponsor as the CRO may have well-defined standards in areas that the sponsor would otherwise have to itself define and develop. Second, users are strictly limited to access standards for only those sponsor organizations for which they have been assigned. For example, Sponsor 1 and Sponsor 2 may establish contractual stipulations that CRO individuals directly assigned to sponsor-specific work may be limited to view only CRO shared standards and sponsor-specific standards for the duration of the contract.

In this respect, User A and User B in the above example are dedicated to Sponsor 1 and Sponsor 2, respectively. CRO oversight personnel (e.g., User C) are configured to have viewing rights to all sponsor standards along with direct access to CRO shared standards. CRO oversight personnel may be configured to have such viewing rights so that they can provide guidance to sponsor-specific users when confronted with difficult standards modeling decisions, and maintain and enhance CRO global standards over time so as to improve the efficiency of sponsor work done by the CRO.

In any event, the CDASH standard may be represented by a declarative XML-based data model conforming to the CDISC Operational Data Model (ODM). The XML-based model facilitates the regulatory-compliant acquisition, archive and interchange of metadata and data for clinical research studies. As one example, a regulatory-compliant standard for exchanging clinical research may be specified in accordance with the CDISC Operational Data Model Version 1.3.2 available from CDISC.ORG. In other examples, one or both of the data tabulation standard and/or the data submission standard may conform to a Study Data Tabulation Model (SD™) data standard and/or an ADaM data standard.

As an example data model, MDR 124 incorporates protocol model 306. The protocol model defines a set of data elements, controlled terminology, and relationships based on existing industry and/or sponsor-specific standards which would be leveraged to automate the transfer and re-use of the same data by different systems. The protocol model enables the platform to be used by different study sponsor organizations and a broad range of vendor types and vendor systems. Foundational industry standards (CDISC (SD™, ODM-XML, CTR-XML, etc.), TransCelerate Common Protocol Template (CPT) libraries, Clinical Trials.gov, EudraCT, HL7/FHIR) are leveraged to define the data elements of the protocol model. The protocol model uses industry standards, such as CDISC, LOINC, SNOMED, MedDRA, ICD9/10, IDMP) to control terminology and relationships to identify additional components from other libraries (CDISC Library, Sponsor Global Libraries) which identify data to be received during defined study time periods which is stored in additional data elements of the protocol model.

MDR 124 implements a full metadata model including various reference libraries, such as Program and Study Design Elements, Objective and Endpoint Templates, Biomedical Concepts, and Study Activities. MDR 124 also holds various clinical data standards, such as Collection Standards, Tabulation Standards, and Analysis Standards. MDR 124 may provide these standards as linked data, including tracing Indication to Objective to Endpoint to Biomedical Concept to Defined Study Activity, and from there further on to Collection, Tabulation, and Analysis Standards. Furthermore, MDR 124 extends the metadata model to include all data elements defined by CDISC Trial Summary Domain and ClinicalTrials.gov specifications.

MDR 124 implements a data model that specifies a data standard representative of requirements for regulatory-compliant exchange of data between entities and stores metadata for the data model. As described herein, the data model includes one or more client business objects. MDR 124 includes data element extensions 308 and metadata extensions 310 that extend the data model set forth in ISO 11179 and/or sponsor-specific standards.

Metadata element extensions 308 include extensions to the business objects to specify one or more study events. Each study activity may be, e.g., a clinical assessment or procedure to be performed on a subject, a data element to be measured from the subject, an assemblage of already existing data about the subject, or collection of non-treatment related data (e.g., healthcare utilization) from the subject. For example, a study event for a study objective may occur on a periodic basis (e.g., daily, weekly, or monthly) and specify a study activity to be performed, for example, that a subject's blood pressure and heart rate be monitored. In accordance with the techniques of the disclosure, a clinical research study may be quantized into a sequence of such study events and study activities, and thereby objectively defined and measured.

Data element extensions 310 extend the data elements of ISO 11179 to include one or more properties for each of the client business objects. MDR 124 may use the properties to organize the client business objects into one or more property groups. Each property specifies a value for a property type for the property. For example, the property type may be one of a date, a time, a string, a uniform resource locator (URL), a Boolean, or an integer. In some examples, one may enumerate one or more valid property types (e.g., as a predefined string or integer list of valid values), where a valid property specifies one of the enumerated property types specified by the predefined list.

In some instances, each of the one or more properties are strongly typed. In some examples, each of the one or more properties specifies a dependent relationship to another property of the one or more properties. In other examples, a property may be compound (i.e., composed of two or more simple properties). Each property group specifies, for example, an ordinality of the property group in a property group hierarchy or a business object within a microservice associated with the property group. In some examples, each property group comprises a clinical research study, a clinical research study protocol, a clinical research study version, a clinical research study design, or a clinical research study.

Properties and property groups are managed as MDR-governed standards and are specified alongside other clinical standards elements, such as CDISC 302 and internal organizational data standards (including sponsor-specific standards). These standards are grouped into a standards collection (i.e., study template) that is managed and versioned within MDR 124. Each version of the standards collection is assigned an Effective Date attribute. MDR 124 uses this Effective Data attribute to automatically select the correct standards collection version to be used as the template for a newly instantiated Study. Properties and property groups are used to implement protocol model 306 as described above. An example property is masking, which has a type Value Domain, so the Masking property in turn references an ISO 11179 Value Domain for Masking, which contains a set of enumerated Domain Values. The enumerated domain values are the only valid values for the value domain masking type, which ensures consistency in metadata across multiple organizations by forcing a user to use only enumerated values when describing data elements.

MDR 124 exposes properties and property groups to applications and microservices via a GraphQL API. With respect to FIG. 1, study design microservice 126 consumes properties and property groups to populate study creation elements. Additionally, Study and Protocol Elements application 116 uses properties and property groups to specify the broad range of data required to fully instantiate a study. A Study Disclosure application may reuse study planning and execution content alongside user-populated study finalization and submission related elements such as governing authority mandates. Further, properties may be configurable elements within objective and endpoint templates used in support of Schedule of Study Activities automation as described herein.

MDR 124 implements properties and property groups as logical class models. Properties are strongly typed, and support property types such as String, URL, Value Domain, Boolean, Date, Timestamp, Time, Integer, Decimal, User, and Compound. Most property types are represented by a LiteralPropertyDefinition subclass. Value Domain properties are represented by a TermPropertyDefinition subclass which references a Terminology Domain (Value Domain) and Terms (Domain Values). Values for term properties may also be dynamically derived via connection to system microservice (e.g., User) or external systems. Compound property types may be composed of two or more simple property types as listed above.

Properties share a set of common configuration elements via a class inheritance structure. Common configuration elements may include, e.g., display name, cardinality, required and multivalued flags, and read-only setting. Each individual type in turn receives type specific elements from its subclass. For example, ordered literal property types such as Integer, Decimal, Date and Timestamp add upper bound and lower bound settings.

Properties may in turn be assembled into Property Groups, where context-specific configuration elements such as ordinality and the associated microservice field name are specified. Property Groups themselves have configuration elements such as display name, and can be assembled by parent groups with each level establishing group-level ordinality as needed.

Properties can also be grouped into dependent relationships. For example, a property specifying a valid set of Indications to be presented when creating a study may depend on a value previously specified for a Therapeutic Area property. Properties can also be grouped into compound assemblies. For example, one may combine a Value Domain property comprising Day, Week, Month, or Year with a positive integer property to represent a study event within the specification of an Endpoint.

Applications 312 of UI framework 102 may invoke metadata extensions 310 to parameterize objective and endpoint templates. In some examples, MDR 124 may further generate, based on the template, one or more study sections each of which is composed of one or more study elements. In some examples, system 100 may further generate, based on the template, at least one study objective and at least one study estimand or endpoint (referred to herein as "endpoint") that may be used to facilitate generation of key activities and events within a schedule of study activities.

These templates parameterize information for scientific hypotheses and link these to associated biomedical concepts and activities that are applicable to those concepts. A clinician may specify objectives and endpoints for the clinical research study based on template constraints, including an identification of study events in support of analysis of the scientific hypotheses. These study events, coupled with the previously mentioned study activities, serve as a basis for automatically generating key aspects of a schedule of activities for the clinical research study. The study activities indicate which clinical observations need to be performed and the study events indicate when these observations need to be scheduled, so that the results of these observations can be used to validate if the study has met the endpoint according to the statistical hypothesis of the study. The clinician may use the generated schedule of activities to guide data collection in support of the scientific hypotheses of the clinical research study.

For example, as described herein, objective and endpoint templates extend the use of properties to support dynamic user-driven objective and endpoint specification within study and protocol elements application 116 of FIG. 1. The objectives and endpoints editor of application 116 presents this templatized information in a structured way such that the clinician can specify key aspects of the study. The specified endpoints are further presented to the clinician in schedule of activities application 114 of FIG. 1. When creating the study events in the schedule using this application, the user is offered suggestions about including certain study events based on the content of the endpoints. These templates are similar to property groups in that the templates contain properties as part of their definition. Objective and endpoint templates include objective or endpoint-specific information, such as objective type, study type, indication (for objective templates), and biomedical concept and associated study activities (for endpoint templates). Objective and endpoint templates further include a tokenized string representing the configurable objective or endpoint text and associated named properties for each of the tokenized string elements.

Study and protocol elements application 116 renders these templates into a configurable form where a user may specify concrete values in combination with template-specific default and read-only values. Study and protocol elements application 116 uses these values, in combination with a parameterized string representation of the Objective or Endpoint, to render a human-readable sentence representing the Objective or Endpoint that is processed by protocol authoring application 118, and in the case of an Endpoint, stored for downstream system use in generating schedule study events and corresponding study activities. Each parameter in the parameterized string is associated with a specific property of the template such that a human readable phrase is produced upon processing of the string and associated properties as specified by the Objective or Endpoint template.

In some examples, a property may be specified as multi-valued (e.g., a property representing a Study Event for which data supporting an Endpoint is to be collected). The human readable phrase rendered from such a configuration may take into account grammatical rules (e.g., if multi-valued secondary Study Event property of an Endpoint template has been specified to include Week 4, Week 8, and Week 12 as values, string rendering processing must produce grammatically correct output such as "The percentage change in HbA1c from Baseline to Week 4, Week 8 and Week 12"). For example, protocol elements application 316 (which may represent an example of study and protocol app 116 of FIG. 1) may invoke properties and property groups to parameterize objective and endpoint templates in the creation of a study. Registration and disclosure application 318 may invoke properties and property groups when generating disclosure submissions mandated by regulatory authorities.

Figure 4:
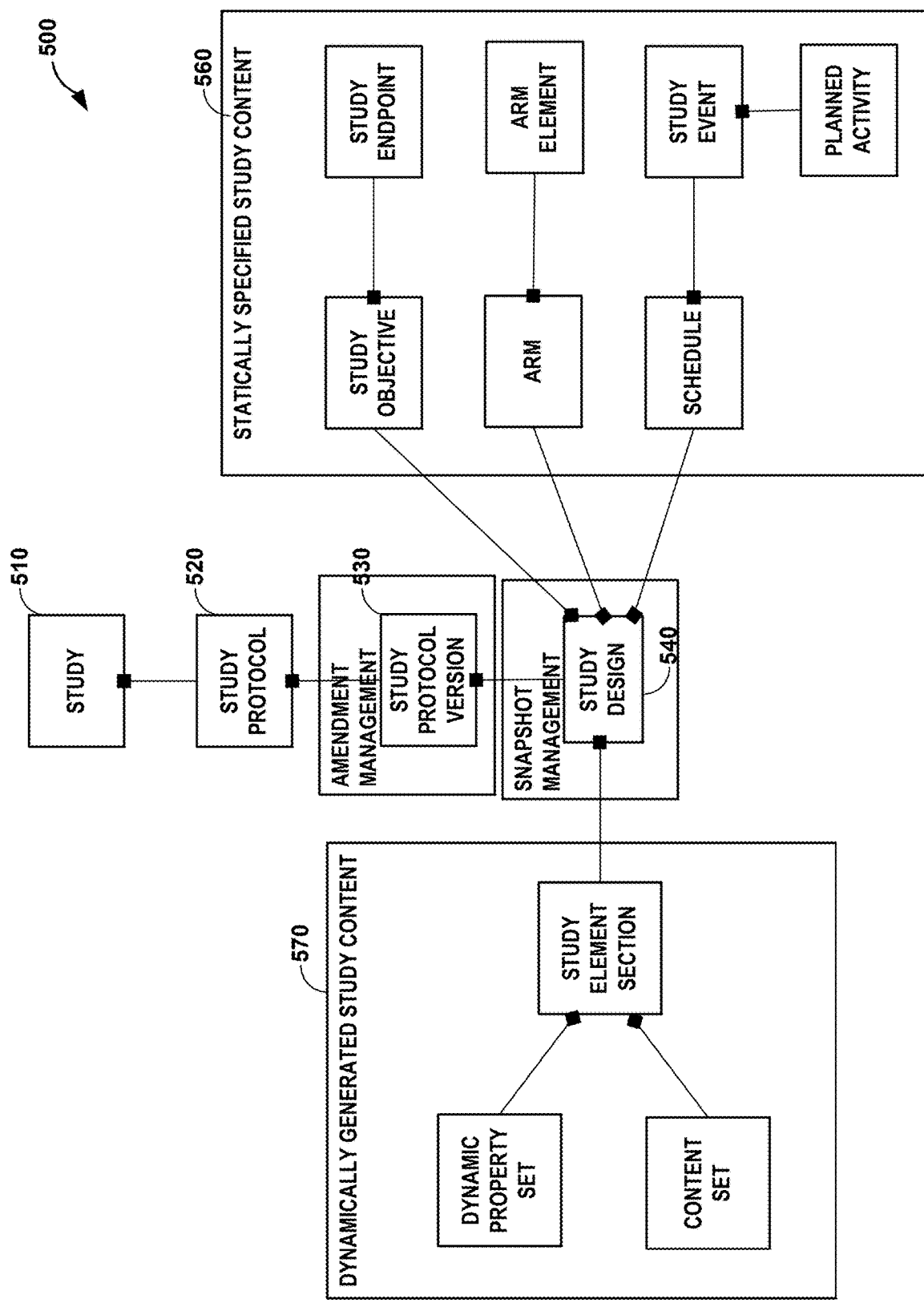
FIG. 4 is a block diagram illustrating an example data system for a clinical research study template in accordance with the techniques of this disclosure.

FIG. 4 is a block diagram illustrating example data system for a clinical research study template in accordance with the techniques of the disclosure. Data system 500 include a number of interconnected data structures 510-560. Study data structure 510 is the entry point to study and protocol content that is managed by Study Design microservice 126 of FIG. 1. Study data structure 510 serves as an anchor point for Study Protocol data structure 520, which binds a corresponding user or users who own a protocol for purposes of attribute-based access control.

Attributes specified during study creation such as Therapeutic Area, Indication, Study Type, Study Phase, Participant Type and Compound may be persisted as part of the Study object and may be used as filter attributes to determine user eligibility for a configured role in system 100. For example, an organization may choose to assign users to specific Therapeutic Areas. As such, each user profile as managed by User microservice 134 will then be populated with one or more Therapeutic Area values for which they are eligible. At time of user login into system 100, Access Control microservice 134 retrieves the set of Therapeutic Area values for the user and incorporates these values into role and permission evaluation.

A user assigned to Therapeutic Area A may, in this example, not be allowed to own, view, or otherwise access Studies created for other Therapeutic Areas. Study data structure 510 includes the following data fields: internalID, ID, owner, protocol, and revision. The foregoing data fields are provided as examples only, and other implementations of the techniques of the disclosure may use only a portion of the foregoing data fields or additional data fields not expressly described herein.

Study protocol data structure 520 serves as an anchor point for the potentially multiple versions of a study that are produced over the life of the study and that system 100 of FIG. 1 manages to implement a digitized protocol. Study protocol data structure 520 may include the following data fields (which may be persisted via dynamic property capabilities in which certain properties are automatically inherited, generated, and/or created due to definition of templates for clinical research studies): internalID, addedOnToExistingTreatments, agencyIDs, aLocation, boardApprovalStatus, caApplicantType, citations, companionStudies, compound, confirmedResponseMinimumDuration, country, currentTherapyOrTreatment, currentVersion, extensionTrialIndicator, ID, Indication, InterventionModel, InterventionModelOtherValue, InvestigationalTherapyOrTreatment, keywords, masking, participant, pharmacologicClass, plannedSubjects, plannedTreamentDuration, plannedTrialDuration, program, protocolNumber, protocolTemplate, pubmedCitationID, responsibleParty, revision, sexOfParticipants, sponsorStatus, stableDiseaseMinimumDuration, stratificationFactor, study, studyDescription, studyPhase, studyStopRules, studyType, studyURL, substudyDetails, substudyPlannedIndicator, supportOrganization, therapeuticArea, trialIntent, trialIntentOtherValue, trialScope, and versions. Again, the foregoing data fields are provided as examples only, and other implementations of the techniques of the disclosure may use only a portion of the foregoing data fields or additional data fields not expressly described herein.

Study protocol version data structure 530 may support a clinical research study template in accordance with the techniques of the disclosure. Study Protocol Version data structure 530 may serve as the anchor point for each version (original or amendment) produced in the course of study planning and execution. Study protocol version data structure 530 includes the following data fields (which similarly may be persisted via dynamic property capabilities in which certain properties are automatically inherited, generated, and/or created due to definition of templates for clinical research studies): internalID, amendment, approvalDate, creationDate, designs, ID, lastModificationDate, ordinal, protocol, protocolAcronym, protocolShortTitle, protocolStatus, protocolTitle, revision, and studyElementObjectID. As noted above, the foregoing data fields are provided as examples only, and other implementations of the techniques of the disclosure may use only a portion of the foregoing data fields or additional data fields not expressly described herein.

Study design data structure 540 may further support a clinical research study template in accordance with the techniques of the disclosure. Study design data structure 540 may serve as the collection of all study protocol version data elements 530, and enables these study protocol version data elements 530 in aggregate to be saved and restored as a snapshot. Snapshots allow users to save their work at checkpoints and if desired return to one of those checkpoints as needed should future study definition work be determined to be incorrect or otherwise problematic. Study design data structure 540 may include the following data fields: internalID, arms, elements, epochs, ID, label, lastModificationDate, lastModificationUser, objectives, ordinal, protocolVersion, revision, schedules, and studyActivities. Once again, the foregoing data fields are provided as examples only, and other implementations of the techniques of the disclosure may use only a portion of the foregoing data fields or additional data fields not expressly described herein.

Study design data structure 560 consists of two primary categories of content: schedule and arm related content, and section-related lock state, properties and comments. Schedule and arm related content consists of Objectives and Endpoints, Arms and Arm Elements, and Schedules, Study Events and Planned Activities. Section-related content consists of Study Element Sections, Dynamic Property Sets and Comment Sets.

In other words, study data structure 510 is (as noted above) the entry point to study and protocol content that is managed by study design microservice 126 of FIG. 1. Study data structure 510 serves as an anchor point for study protocol data structure 520 and contains mandatory data fields (which may be another way to refer to "study design elements") specified during study creation such as Therapeutic Area, Indication, Study Type, Study Phase, Participant Type and Compound. These attributes characterize the study and are thus immutable upon study creation. They may also be used to assist, via attribute-based access control mechanisms implemented by system 100, in binding specific users to the study.

In some instances, attribute-based access control enables use of these attributes within filters that are then used to determine user eligibility for a configured role (e.g., study owner, study protocol editor, etc.) in system 100. For example, an organization may choose to assign users to specific Therapeutic Areas. As such, each user profile as managed by user microservice 134 will then be populated with one or more Therapeutic Area values for which the associated users are eligible. At time of user login into system 100, access control microservice 134 retrieves the set of Therapeutic Area values for the user and incorporates these values into role and permission evaluation. In this manner, a user assigned to Therapeutic Area A in this example is not allowed to own, view, or otherwise access Studies created for other Therapeutic Areas. The foregoing data fields discussed above are provided as examples only, and other implementations of the techniques of the disclosure may use only a portion of the foregoing data fields or additional data fields not expressly described herein.

Study protocol data structure 520 represents an anchor point for potentially multiple versions of a study protocol that are produced over the life of the study and that system 100 of FIG. 1 manages to implement a digitized protocol. As such, study protocol data structure 520 contains an immutable Protocol Number data field that is specified at time of study creation, along with a collection of all study protocol versions in existence for the study and specific references to the original and currently active study protocol version. The foregoing data fields are provided as examples only, and other implementations of the techniques of the disclosure may use only a portion of the foregoing data fields or additional data fields not expressly described herein.

Study protocol version 530 represents an anchor point for each version (original or amendment, and minor versions of the same) produced in the course of study planning and execution. As such, the study protocol version data structure includes the following data fields: amendment version (major and minor), creation date, approval date, and mutable study protocol attributes such as protocol title, protocol short title, protocol acronym and protocol keywords. Study protocol version also maintains a reference to the currently active study design along with a collection of all study designs in existence for the study protocol version. The foregoing data fields are provided as examples only, and other implementations of the techniques of the disclosure may use only a portion of the foregoing data fields or additional data fields not expressly described herein.

Study design data structure 540 may serve as the collection of all Study Protocol Version data structures and elements, and enables these data structures and elements in aggregate to be saved and restored as a snapshot. Snapshots allow users to save their work at meaningful checkpoints and if desired return to one of those checkpoints as needed should future study definition work be determined to be incorrect or otherwise problematic. Only the currently active study design as referenced by the study protocol version may be updated in the course of study protocol development.

Study design content can be further classified into one of two content categories: statically specified (or in other words, fixed) study protocol elements (shown as statically specified study content 560) and dynamically generated elements (shown as dynamically generated study content 570). For example, statically-specified study content 560 may include Objectives and Endpoints, Arms and Arm Elements, and Schedules, Study Events and Planned Activities, each of which supports aspects of study design as discussed throughout this disclosure. Dynamically generated study content 570 may include a representation of section-related content via Study Element Sections. Each Study Element Section may in turn consist of a section locked element, Dynamic Property Sets and Comment Sets. A Dynamic Property Set represents the manifestation of a specific dynamic property group with its collection of dynamically configured properties as discussed throughout this disclosure. A Comment Set represents a collection of informal thread-based communications created by Study role-players as appropriate to assist in section specification decisions made over the course of Study Element Section development and review. The foregoing data fields are provided as examples only, and other implementations of the techniques of the disclosure may use only a portion of the foregoing data fields or additional data fields not expressly described herein.

The section locked element of a Study Element Section is used in combination with user access control permissions to control the ability to update the content of the associated section, and can also be used to validate whether updates to related sections are allowed (e.g., a user who has update permission for the Schedule section may still be prevented from editing that section until the Arms section is locked; a user attempting to submit a Study Protocol Version for approval may be prevented from that submission if Lean Protocol is installed and the Lean Protocol section is unlocked). In support of these and other permissions validation requirements, the Study Design service integrates a configurable rules engine. For example, when a user attempts to update a specific Study Element Section, the rules engine looks up the section, verifies that it is under a Study Protocol Version that is not in an approved state, checks that the properties in the section are valid, and then does an Access Control check to make sure the user has permission to lock the section.

In this way, dynamically generated study content 570, which includes dynamic property set, comment set, and study element section, are dynamically configured from MDR 124, where property and property groups flow from MDR 124 (e.g., MDR 124 provides the structure, users enter information with respect to such structure, and MDR 124 dynamically persists the information entered by the users via a dynamic properties microservice). MDR 124 may, in other words, specify properties and/or property groups as key-value pairs so that such properties and/or property groups can be resolved into a cohesive object. For example, 100 or more attributes (which is another way to refer to properties) may result in a single object type.

In addition, the template represented by data system 500 (and which may, as a result, be referred to as template 500) may parameterize what normally would be entered as a text phrase (e.g., in a document defining a study). For example, a scientific hypothesis specification may be entered (e.g., "To evaluate the efficacy of ZD 5 mg Daily/Oral administered to individuals with Type 2 Diabetes Mellitus (T2DM) "), whereupon study design microservice 126 may parse such text phrase representative of the scientific hypothesis specification to identify parameters by which to identify attributes to which system 100 may automate against. Study design microservice 126 may generate endpoints as part of statically specified study content 560, where in the example above such endpoints may include "The absolute change in HbA1c from Baseline to Week 4, Week 8 and Week 12), "The percentage of patients with HbA1c (%)<10% at Week 10," etc.

Study and protocol elements user interface 116 may enable editing of objectives and definition of different endpoints to facilitate dynamic generation of the study. In the immediately preceding examples, the values "Baseline", "Week 4", "Week 8", "Week 10", and "Week 12" represent Study Events that may be automatically populated into a Schedule for the Study. The edits all flow to template 500 and create additional arms, arm elements, schedules, events, activities, etc, as described above. Study design 540 may control which of the created events, activities, etc. are to be performed and/or edited, using template 500 as a definition for mandatory activities and events, thereby allowing template 500 from MDR 124 to establish secure and safe clinical research studies that adhere to formal and/or sponsor standards while also potentially permitting expedient study research as such templates may be reusable and allow for faster study design.

Figure 5:
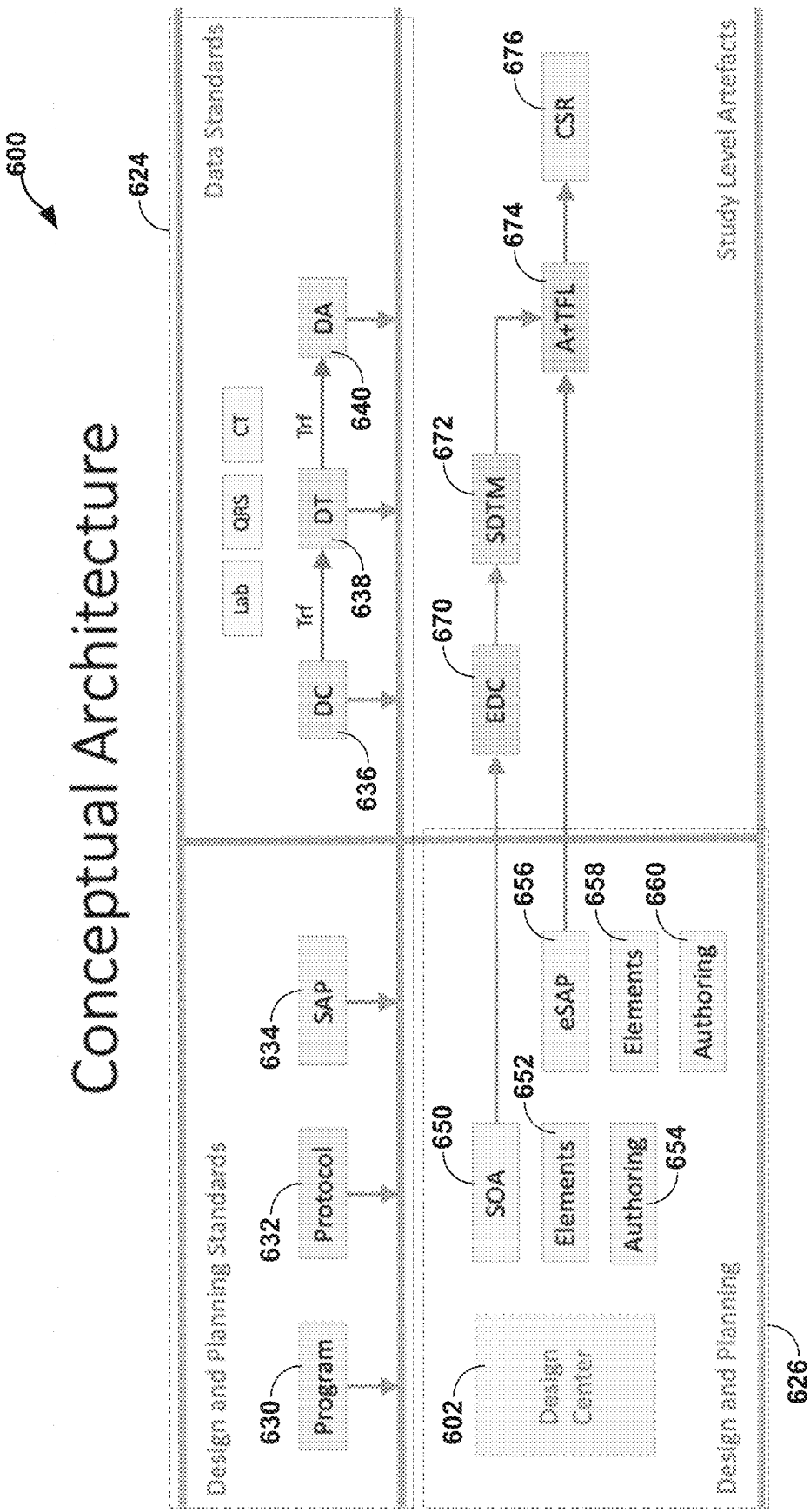
FIG. 5 is a diagram illustrating a conceptual architecture of the system shown in the example of FIG. 1 in supporting the code generation microservice to perform various aspects of the techniques described in this disclosure.

FIG. 5 is a diagram illustrating a conceptual architecture of the system shown in the example of FIG. 1 in supporting the code generation microservice to perform various aspects of the techniques described in this disclosure. As shown in the example of FIG. 5, architecture 600 includes a standards conceptual level 624 (which is represented in the example of system 100 shown in FIG. 1 as MDR 124) and a design and planning conceptual level 626 (which is represented in the example of system 100 as study design microservice 126).

Standards conceptual level 624 specifies program standards 630, protocol standards 632, and statistical analysis plans (SAP) standards 634. Program 630 defines standards for a number of different clinical development programs, while protocol standards 632 define a number of different standards for clinical research study protocols. SAP 634 may specify various statistical analysis plan standards that define processes and statistics for measuring the success of a clinical research trial.

Standards conceptual level 624 may also include clinical data standards involving data collection (DC) standards 636, data tabulation (DT) standards 638, and data analysis (DA) standards 640. Data collection standards 636 may specify various standards involved in data collection, including how the data is to be captured and all the variables (including variable names) and the like. Data tabulation standards 638 may specify how the collected data is to be tabulated, while data analysis standards 640 indicate how the collected data is to be analyzed. Standards conceptual level 624 may specify various transformations (Trf) for transforming collected data between DC standards 636 and DT standards 638 and between DT standards 638 and DA standards 640.

Design and planning conceptual level 626 includes a design center 602 representative of portions of UI framework 102 shown in the example of FIG. 1 in designing and planning a particular clinical research study that results in schedule of activities (SOA) 650, study elements 652 ("elements 652), and authoring 654. Design center 602 may also, through interactions with a user, generate an electronic statistical analysis plan (eSAP) 656, along with additional elements 658, and authoring 660.

Given SOA 650, architecture 600 may produce an electronic data capture 670 (using pertinent DC standards 636) and a standards data tabulation model 672. CG microservice 150 may process SOA 650 (as represented by EDC 670) along with metadata (stored in standards conceptual level 624) necessary to create SDTM 672, to generate the first and second mappings noted above that are used to form transformations may transforming collected data between EDC 670 and SDTM 672.

System 100 may also automate generation of a data analysis, including tables, figures, and listings (A+TFL) 674 based on eSAP 656 and SDTM 672 (which again may be informed by DA standards 640 pertinent to SDTM 672 for the particular clinical research study defined by SOA 650. System 100 may further support the authoring of, based on A+TFL 674, a clinical study report (CSR) 676.

Figure 6:
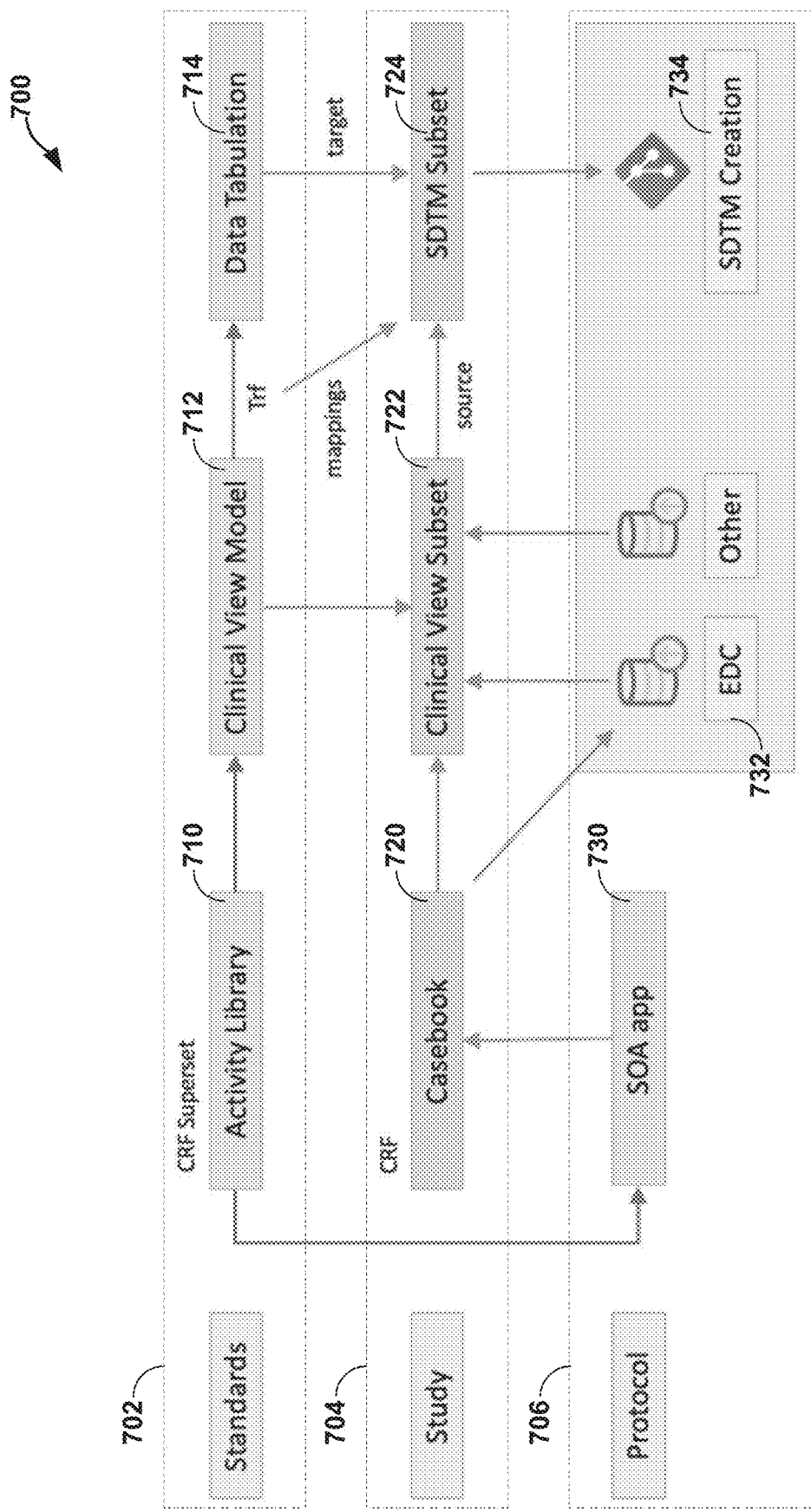
FIG. 6 is a diagram illustrating another conceptual architecture for the system shown in the example of FIG. 1 in supporting automatic generation of transformations between electronic data capture and the standards data model in accordance with various aspects of the techniques described in this disclosure.

FIG. 6 is a diagram illustrating another conceptual architecture for the system shown in the example of FIG. 1 in supporting automatic generation of transformations between electronic data capture and the standards data model in accordance with various aspects of the techniques described in this disclosure. In the example of FIG. 6, an architecture 700 includes a standards layer 702, a study layer 704, and a protocol layer 706.

Standards layer 702 may represent a layer in which system 100 defines all elements for most if not all potential studies. That is, standards layer 702 defines global standards regardless of the particular clinical research study being designed. For example, standards layer 700 may specify how heart rate data is collected and a variable name associated with collected heart rate data.

Standards layer 702 may include, for example, an activity library 710, a clinical view model 712, and data tabulation 714. Activity library 710 defines a number of different activities that can be performed in support of most if not all clinical research studies. Clinical view model 712 defines standards for how clinical research data is stored after collection for each particular activity presented in activity library 710. Data tabulation 714 provides standards for data tabulation of clinical research data populated in clinical view model 712.

System 100, as conceptually represented by architecture 700, defines the schedule of activities (SOA) 730 (at protocol layer 706) for a particular study, selecting activities from activity library 710 pertinent to the particular study. Once system 100 generates SOA 730, system 100 may generate a clinical research form in the form of a casebook 720 as shown in study layer 704. System 100 may generate, based on casebook 720, EDC 732 (which is present at protocol layer 706). EDC 732 may present variables representative of collected data as so-called "views."

Given that casebook 720 defines the study, system 100 may select a subset of clinical view model 712 that are required by casebook 720 to conduct clinical research. The selected subset of clinical views from clinical view model 712 is shown as clinical view subset 722. Clinical view subset 722 may define the metadata that are being collected for the particular study.

System 100 may also generate, based on clinical view subsets 722 and data tabulation 714, SDTM subset 724. SDTM subset 724 defines one or more domains for data tabulation required for the particular study. Domains may define types of data, such as vital signs, adverse effects, etc. Each domain contains all of the collected data for each type of domain, like vital signs, adverse effects, etc.

CG microservice 150 may obtain a source in the form of clinical view subset 722 (as defined by study design microservice 126) and a target in the form of SDTM subset 724 (as defined by MDR 124). CG microservice 150 may next obtain transformations between the source and target, where such transformations may be defined by MDR 124. CG microservice 150 may obtain the subset of transformation defined by MDR 124 pertinent to the particular study as defined by clinical view subset 722 and SDTM subset 724. SD™ subset 724 may represent the selected subset of the transformation for converting or otherwise transforming the source (the variables defined in support of clinical view subset 722) to the target (the domains defined in support of SDTM subset 724). Based on SD™ subset 724, system 100 may perform SDTM creation, as denoted by SDTM creation 734.

Figure 7:
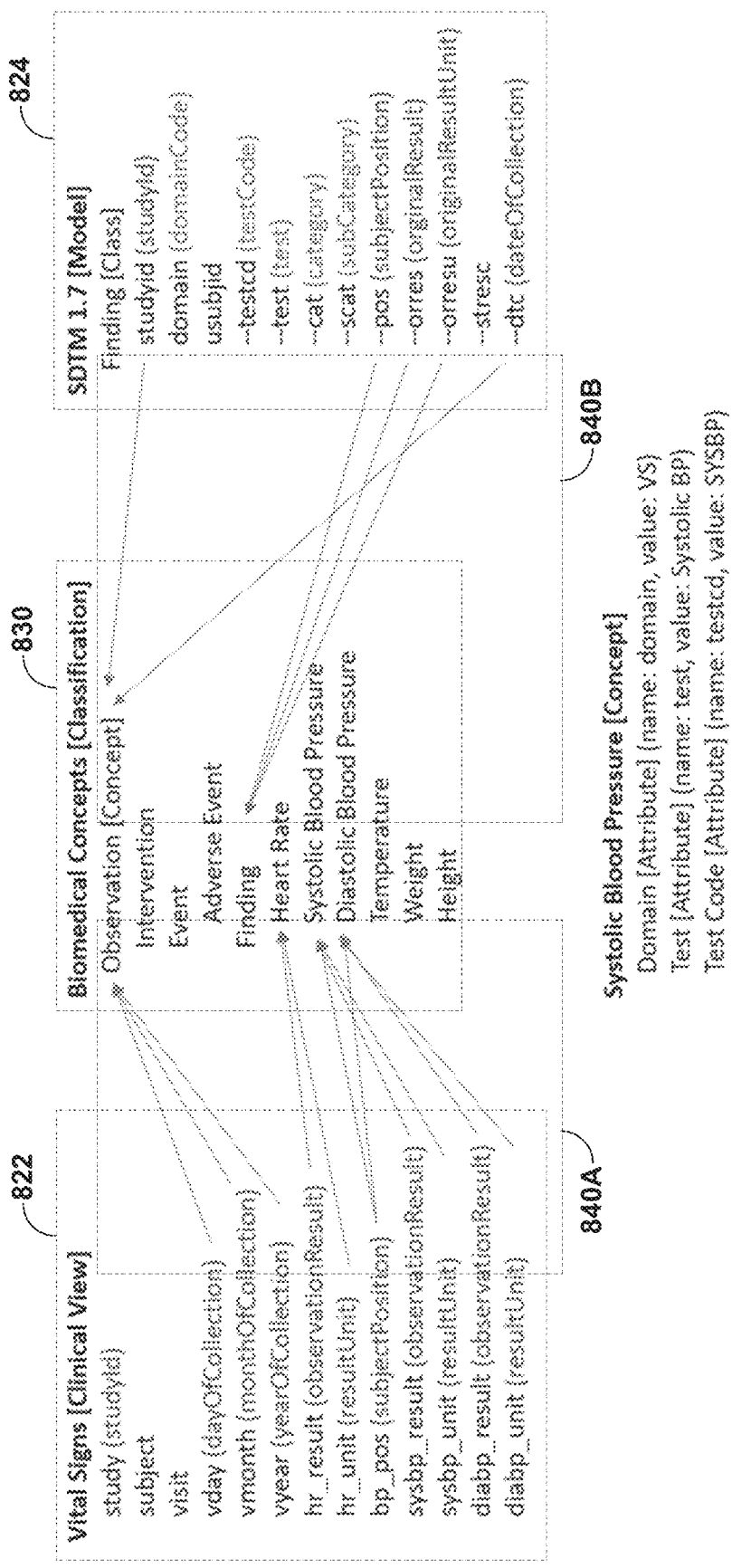
FIGS. 7 and 8 are diagrams illustrating automatic generation of transformation by code generator microservice shown in the example of FIG. 1 in accordance with various aspects of the techniques described in this disclosure.
Figure 8:
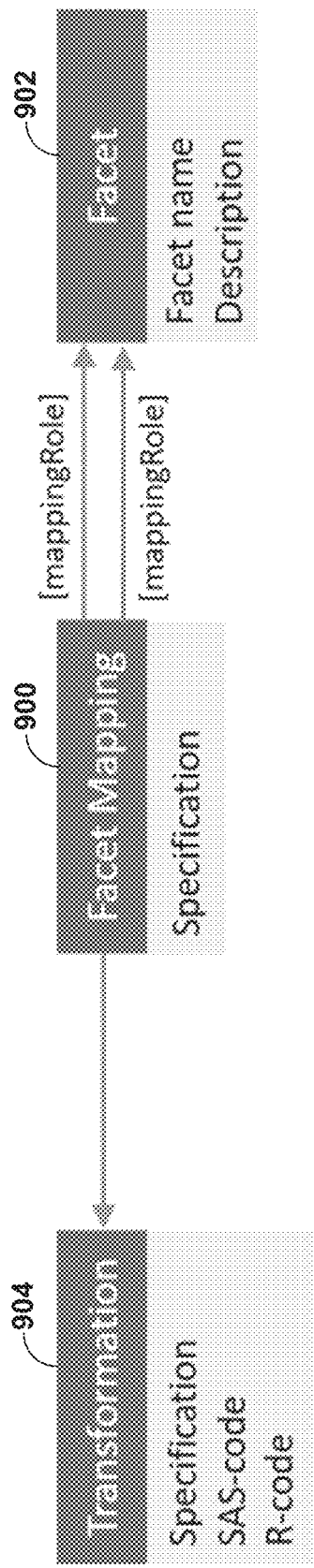

FIGS. 7 and 8 are diagrams illustrating automatic generation of transformation by code generator microservice shown in the example of FIG. 1 in accordance with various aspects of the techniques described in this disclosure. In the example of FIG. 7, client view subset 822 represents one example of client view subset 722 shown in the example of FIG. 6, while SDTM model 824 represents one example of SDTM subset 724 also shown in the example of FIG. 6.

Client view subset 822 includes various views defining vital signs. These vital sign include various source variables such as a study, a subject, a visit, a visit day ("vday"), a visit month ("vmonth"), a visit year ("vyear"), a heart rate result ("hr_result"), a heart rate unit ("hr_unit"), a blood pressure position ("bp_pos"), a systolic blood pressure result ("sysbp_result"), a systolic blood pressure unit ("sysbp_unit"), a diastolic blood pressure result ("diabp_result"), and a diastolic blood pressure unit ("diabp_unit").

A number of different variables are also tagged with facets that indicate a type of the collected data. The "study" variable is tagged with a study identifier ("studyId") facet. The source "vday" variable is tagged with a day of collection ("dayOfCollection") facet. The source "vmonth" variable is tagged with a month of collection ("monthOfCollection") facet, and so on. Each source variable tagged with a facet denotes the facet in the parenthetical specified next to the source variable name.

STDM model 824 includes classes having target variables. In the example of FIG. 8, STDM model 824 includes a "Finding" class in which target variables are shown as studyId, domain, and usubjid, which includes sub-variables that include, as an example, test code ("testcd"), test, category ("cat"), sub-category ("scat"), subject position ("pos"), original result ("orres"), original result unit ("orresu"), standard result in character format ("stresc"), and date of collection ("dtc"). Similar to the source variables of client view subset 822, a number of target variables may be tagged with facets. For example, target study variable is tagged with facet "studyId," target position variable "pos" is tagged with the "subjectPosition" facet, the target original result variable "orres" is tagged with the "originalResult" facet, the target orresu variable is tagged with the "originalResultUnit" facet, and the target "dtc" variable is tagged with the facet "dateOfCollection." Each target variable tagged with a facet denotes the facet in the parenthetical specified next to the target variable name.

As noted above, the user, via UI framework 102, may map source variables to one or more concept 830 and likewise map target variables to one or more concept 830. Concept 830 represents an intermediate classification that facilitates automatic transformation between source variables supporting clinical view model 822 and target variables supporting SD™ model 824.

In the example of FIG. 7, concept 830 includes a "Biomedical Concept," which is a hierarchical arrangement of concepts with an "Observation" concept forming the highest hierarchy under which "Intervention," "Event," and "Finding" concepts are arranged. Under the Event concept, there is an "Adverse Event" sub-concept, while the "Finding" concept includes further sub-concepts shown as "Heart Rate," "Systolic Blood Pressure," "Diastolic Blood Pressure," "Temperature," "Weight," and "Height."

As shown at the bottom of FIG. 7, the "Systolic Blood Pressure" concept has an attribute with a domain name having a value of "VS" for vital signs, which is a type of dataset into which to map the "Systolic Blook Pressure" concept. Additional attributes may be defined, such as a "Test" attribute with the name "test" and a value of "Systolic BP," and a "Test Code" attribute with the name "testcd" and a value of "SYSBP." These concepts represent a library of transformations (or, in other words, mappings) on how to map concepts into SDTM model 824.

The user, via UI framework 102, may associate source variables of clinical view subset 822 to concepts 830 to generate first mappings 840A (which are denoted as arrows). The user, again via UI framework 102, may associate target variables of SDTM model 824 to concepts 830 to generate second mappings 840B (which again are denoted as arrows). CG microservice 150 may generate, based on first mappings 840A and second mappings 840B, the transformational data defining the transformation of collected data stored as source variables in support of client view subset 822 to target variables supporting SDTM model 824.

Referring next to the example of FIG. 8, CG microservice 150 uses facet names to generate first mapping 840A and second mapping 840B. For example, consider the source "vday," "vmonth," and "vyear" variables that are tagged with different respective facet names "dayOfCollection," "monthOfCollection," and "yearOfCollection," each of which are mapped per first mappings 840A to the "Observation" concept of concepts 830 as shown in the example of FIG. 8. The target "dtc" variable with a facet of "dateOfCollection" is also mapped via mappings 840B to the same "Observation" concept of concepts 830. The input, or in other words, source facet names for the above noted example source variables are mapped to the target "dtc" variable name of SDTM model 824 via the "Observation" concept of concepts 830.

CG microservice 150, using this facet mapping, searches the transformation stored to MDR 124 to identify a "dateOfCollection" mapping. Assuming CG microservice 150 identifies the "dateOfCollection" mapping, CG microservice 150 determines that the three input facets "dayOfCollection," "monthOfCollection," and "yearOfCollection" are used to generate the "dateOfCollection" output (or, in other words, target) facet associated with variable "dtc." CG microservice 150 then confirms that the three source variables associated with the source facets are available, and responsive to confirming that the three source variables associated with the source facets are available, generates transformational data defining the transformation from the source variables to the target variable.

Generally, as shown in the example of FIG. 8, CG microservice 150 identifies facet mappings 900, which define a mapping between input (or in other words, source) facets and output (or in other words, target) facets. CG microservice 150 may next confirm that the source and target facets are available via facet name descriptions 902 for the source data and the target data (as represented by the source and target variables stored to client view subset 822 and SDTM model 824). Assuming both the source and target facets align with facet mapping 900, CG microservice 150 may generate transformational data 904 defining a transformation in one or more of a specification, SAS code, and/or R code.

CG microservice 150 may generate example transformational data as follows for the collection date facet mapping:

---

Facet Mappings
EDC to SDTM collection date [Facet Mapping]
   Input Facet
      dayOfCollection [Facet] (mappingRole: $.day)
      monthOfCollection [Facet] (mappingRole: $.month)
      yearOfCollection [Facet] (mappingRole: $.year)
   Output Facet
      dateOfCollection [Facet] (mappingRole: $.date)
   Transformation
      edc2iso8601date [Transformation] (SAS-code: %edc2iso8601
      ($.day, $.month, $. year, $.date))

---

In the above example, CG microservice 150 may populate the $.day parameter with the variable name associated with input facet dayOfCollection, which in this example is "vday." Likewise, CG microservice 150 may populate the $.month parameter with the variable name associated with input facet monthOfCollection, which in this example is "vmonth." CG microservice 150 may populate the $.year parameter with the variable name associated with input facet yearOfCollection, which in this example is "vyear." CG microservice 150 will also populate the $.date parameter with the variable name associated with output facet dateOfCollection, which in this example is "dtc." CG microservice 150 will output transformational data conforming to the "Transformation" denoted above as SAS code that transforms vday, vmonth, vyear into dtc.

Using facets in this manner may enable increased efficiency when defining additional data to be collected. Consider, returning to the example of FIG. 8, that the study has been updated to collect a body mass index (BMI) of patients undergoing the study. To add BMI to client view subset 822, the user may define (possibly indirectly via interactions with study design microservice 126) a "bmi_result" variable with an "observationResult" facet, which is the same facet assigned to hr_result and other variables. The user may also add (again, possibly indirectly via interactions with study design microservice 126) a "bmi_unit" variable with a "resultUnit" facet. As these "observationResult" and "resultUnit" facets have been previously mapped to Observation, system 100 may automatically map the bmi_result and bmi_unit variables to the Observation concept.

There is no need to update SDTM model 824 to accommodate the addition of BMI, as the orres and orresu variables in SDTM model 824 were previously defined and may be used for each of the variables of clinical view subset 822 mapped to the Observation concept. As such, CG microservice 150 may operate as noted above to create transformational data similar to transformational data 904, populating the correct variable names in place of the parameters.

Figure 9:
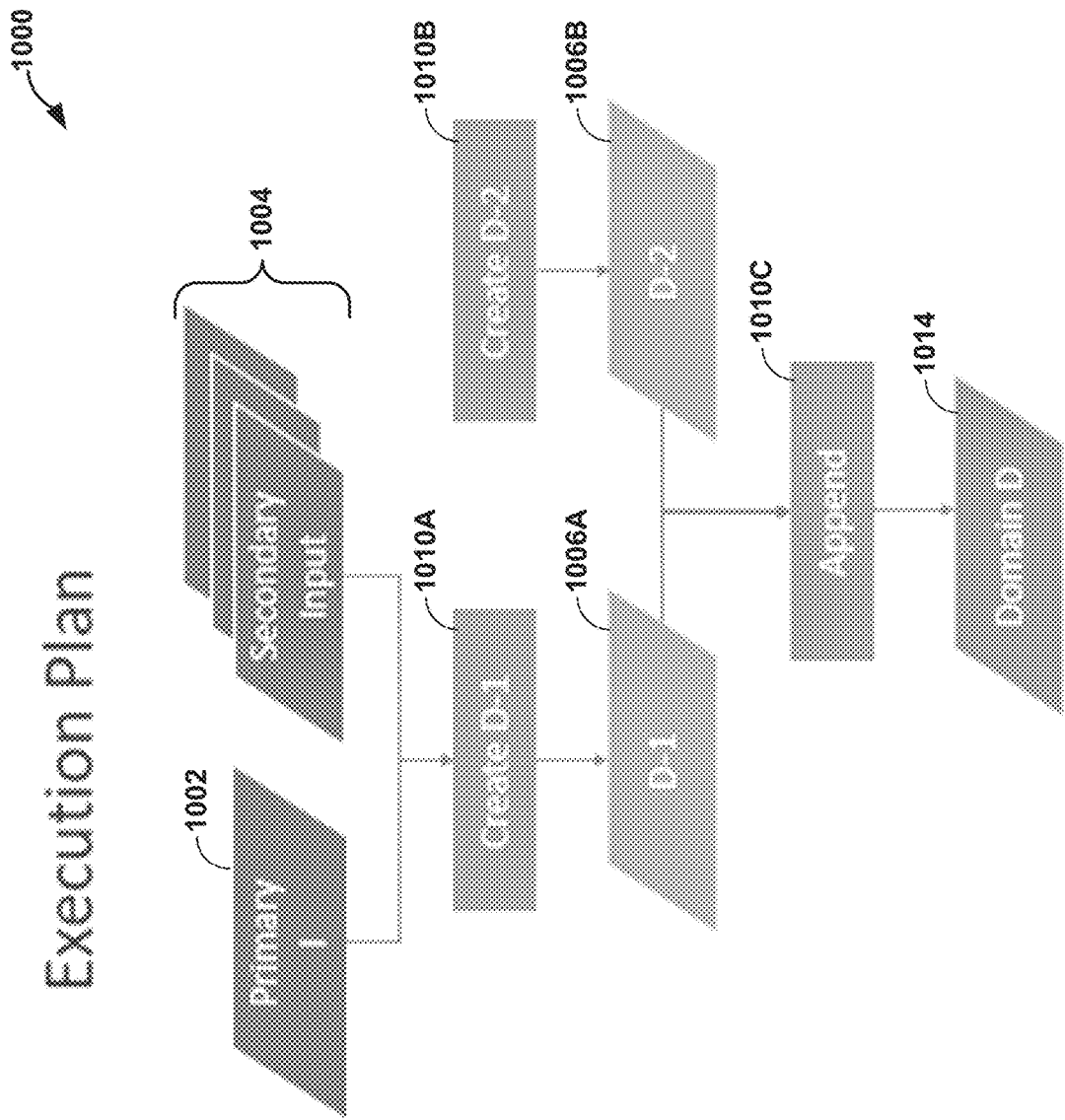
FIG. 9 is a diagram illustrating operation of the code generator shown in the example of FIG. 1 in performing automatic transformation generation in accordance with various aspects of the techniques described herein.

FIG. 9 is a diagram illustrating operation of the code generator microservice shown in the example of FIG. 1 in performing automatic transformation generation in accordance with various aspects of the techniques described herein. In the example of FIG. 9, CG microservice 150 may, prior to generating the transformational data in the manner described above, form an execution plan 1000. CG microservice 150 may generate execution plan 1000 in the form of a data structure, such as a tree data structure, a graph data structure, and/or the like.

CG microservice 150 may first traverse all metadata to identify a list of all clinical views in a clinical view subset, such as clinical view subset 722 and/or 822, and a list of target SDTM domains, such as SDTM subset 724 and/or SDTM model 824. CG microservice 150 may then lookup, in the clinical views, all of the source variables that are associated with a given concept. CG microservice 150 may then determine, based on the given concept, domains within SDTM subset 724 that are associated with the concept.

Figure 10:
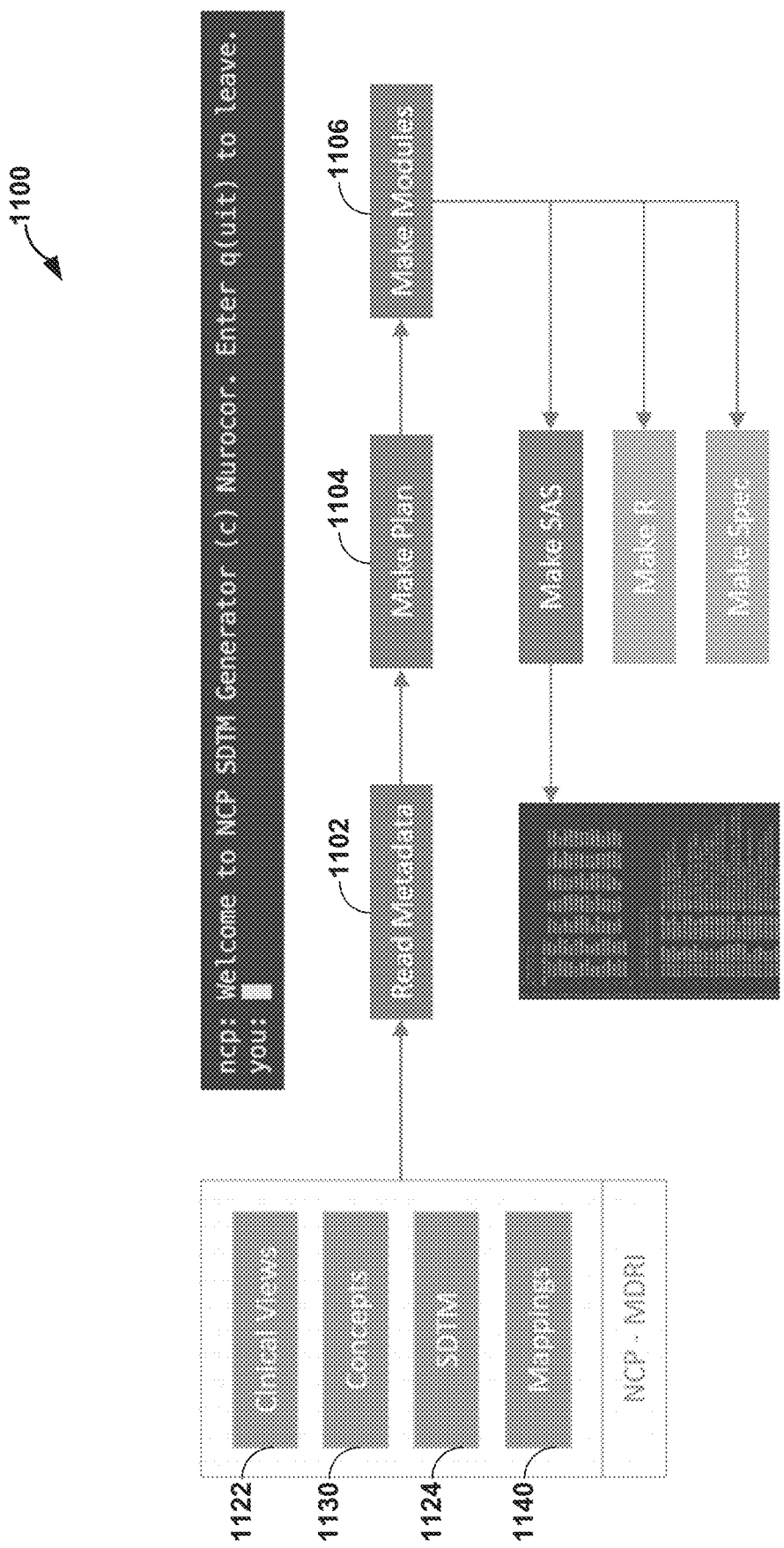
FIG. 10 is a diagram illustrating how the code generator microservice shown in the example of FIG. 1 processes various metadata to automatically generate transformations in accordance with various aspects of the techniques described in this disclosure.

In the example of FIG. 10, CG microservice 150 may identify input variables from various sources, e.g., primary input ("I") source 1002 and secondary input sources 1004. CG microservice 150 may generate a domain D-1 1006A that maps sources 1002 and 1004 to domain D-1 1006A. CG microservice 150 may also generate a domain D-2 1006B (and possible additional sub-domains, such as domain D-3, etc., which are not shown for ease of illustration purposes). CG microservice 150 may resolve all of these dependencies and generates an execution plan 1000.

CG microservice 150 may then generate transformational data 1010A to transform sources 1002 and 1004 to domain D-1 1006A and thereby "Create D-1." Likewise, CG microservice 150 may also generate transformational data 1010B to transform sources (not shown in the example of FIG. 10 for ease of illustration purposes) to domain D-2 1006B. CG microservice 150 may, after defining transformational data 1010A and 1010B to create domains D-1 1006A and D-2

1006B, generate additional transformational data 1010C to append domain D-2 1006B to domain D-1 1006A to generate a domain D 1014. transformational data 1010A, 110B, and 1010C may be defined as separate programs (or in other words, executable code), as a single program, or some combination thereof.

Although described with respect to a single clinical view, CG microservice 150 may identify multiple clinical views that contribute to the same domain (such as vital signs). The data collected for the different clinical views may have the same or possibly a different format. In addition, the data could be captured from different sources, where for example, some data may be captured on the case report form (CRF) while other data may be captured from a lab or multiple labs.

FIG. 10 is a diagram illustrating how the code generator microservice shown in the example of FIG. 1 processes various metadata to automatically generate transformations in accordance with various aspects of the techniques described in this disclosure. CG microservice 150 may, as shown in the example of FIG. 10, perform a process 1100 to initially read metadata (1102) from MDR 124, where such metadata may include clinical views 1122 (which is an example of clinical view subsets 722 and/or 822), concepts 1130 (which is an example of concepts 830), SDTM 1124 (which is an example of SDTM subset 724 and/or SDTM model 824), and mappings 1140 (which is an example of mappings 840).

CG microservice 150 may next make a plan (1104), such as execution plan 1100, which results in making modules (1106), such as transformational data 1010A, 110B, and/or 1010C. The result of making such modules is one or more of SAS code, R code and/or a specification ("Spec"). This code may include comments that provide details regarding the transformation, where CG microservice 150 may copy such comments from mappings 1140. CG microservice 150 may output transformational data 1010A, 1010B and/or 1010C for execution at a user premises or other location (e.g., a datacenter) that stores sensitive patient data.

Figure 11:
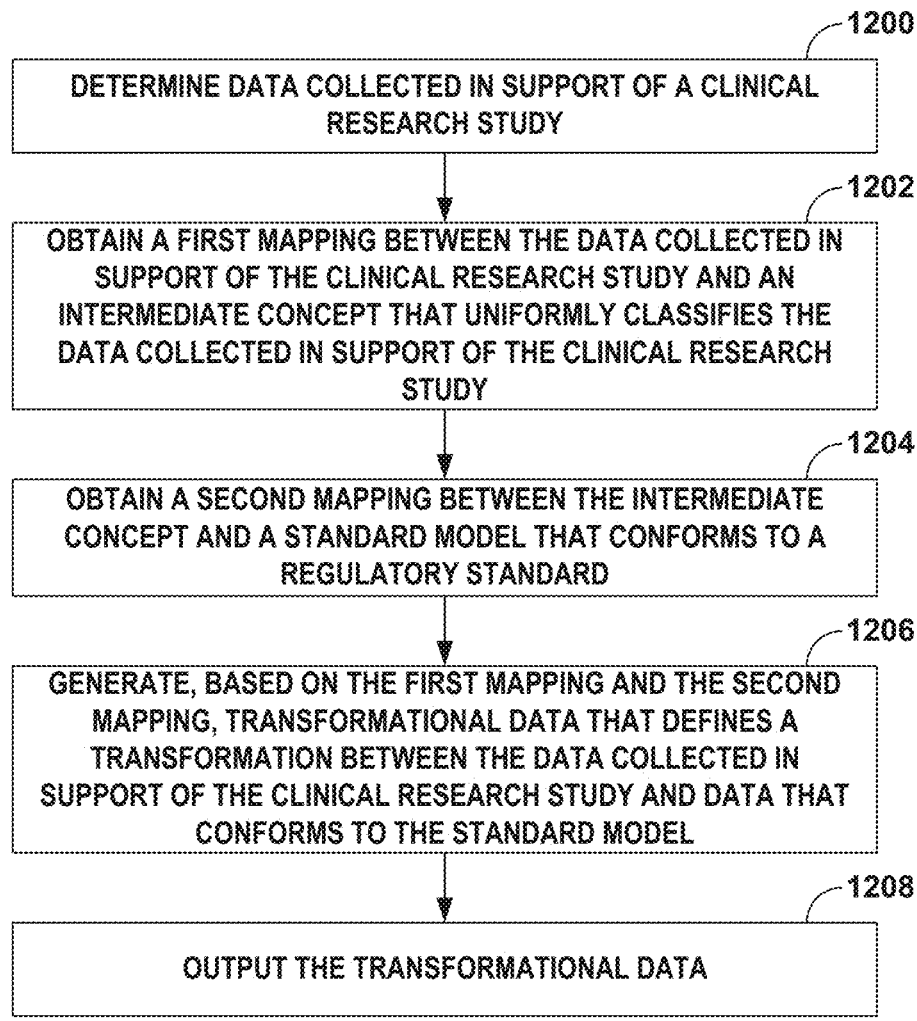
FIG. 11 is a flowchart illustrating example operation of the code generator microservice in performing various aspects of the techniques described in this disclosure.

FIG. 11 is a flowchart illustrating example operation of the code generator microservice in performing various aspects of the techniques described in this disclosure. As described above, CG microservice 150 may determine data collected in support of a clinical research study. That is, CG microservice 150 may determine, based on the above noted schedule of activities for the study protocol, the data collection elements captured in support of the clinical research trial (1200).

CG microservice 150 may traverse the schedule of activities and identify study events having study activities associated with different types of data, where such data may be denoted using variables (or, in other words, variable names). The data collected in support of the clinical study may conform to clinical data standards that defines how the data is to be captured and mapped to the underlying variable names. CG microservice 150 may further determine a data collection type of the data collected in support of the clinical research study. This data collection type may be referred to herein as a "facet," which provides a uniform classification or, in other words, type of the collected data. For example, a variable for the visit data denoted as "vday" may have an assigned facet of "dayOfCollection."

CG microservice 150 may, based on these variables and facets, obtain a first mapping between the data collected in support of the clinical research study and an intermediate concept that uniformly classifies the data collected in support of the clinical research study (1202). Via UI framework 102, a user may specify these mappings between variable/facet pairs and the intermediate concept. In the example above, a user may map vday (dayOfCollection) to an Observation concept. Additional variables may be mapped to the Observation concept, such as visit month denoted as "vmonth" having a facet of monthOfCollection or visit year denoted as "vyear" having a facet of yearOfCollection.

CG microservice 150 may next obtain a second mapping between the concepts and the standard model (which may also be referred to as a standard data model) that conforms to the regulatory standard (1204). The standard data model may include elements, such as "dtc" which refers to the date of collection and is assigned to the dateOfCollection facet. CG microservice 150 may access MDR 124 to identify these standard data model elements with little to no human oversight. Via UI framework 102, a user may assign the facets to the standard data model elements in order to define potential transformations at a high semantic level using the intermediate concepts to link facets of variables to facets of standard data model elements. CG microservice 150 may then resolve the second mapping using the similar facets that map to the same intermediate concept. As discuss in further detail above, this definitional framework for associating variables by way of associated facets between intermediate concepts that are associated with standard data model elements having the same facet may result in reuse and further automation of the underlying transform.

In any event, CG microservice 150 may generate, based on the first mapping and the second mapping, transformational data that defines a transformation between the data collected in support of the clinical research study and data that conforms to the standard model (1206). CG microservice 150 may generate intermediate data structures to resolve how collected data will be transformed in terms of order with respect to different variables and data sources and/or settings. CG microservice 150 may then generate the transformational data based on the intermediate data structures defining the order of transformation to form cohesive data sets that conform to the regulatory standards, outputting the transformational data for use.

That is, system 100 may not store the actual collected data, but rather symbolically represent the collected data in terms of the variables. Personal health data and any other types of research data may require robust security and compliance with a number of different regulatory standards to ensure patient/test subject privacy. System 100, while potentially adaptable for storing such sensitive data, may not provide sufficient security while also facilitating the study development process by a wide number of different study designers. As such, CG microservice 150 may output the transformation data for execution by users of system 100 at a local repository that stores the collected data and that is subject to more secure environments that complies with the various regulatory standards surrounding sensitive personal health data (1208).

As such, various aspects of the techniques may enable one or more of the following examples.

Example 1. A method comprising: determining, by a code generator executed by processing circuitry, data collected in support of a clinical research study; obtaining, by the code generator, a first mapping between the data collected in support of the clinical research study and an intermediate concept that uniformly classifies the data collected in support of the clinical research study; obtaining, by the code generator, a second mapping between the intermediate concept and a standard model that conforms to a regulatory standard; generating, by the code generator and based on the first mapping and the second mapping, transformational data that defines a transformation between the data collected in support of the clinical research study and data that conforms to the standard model; and outputting, by the code generator, the transformational data.

Example 2. The method of example 1, wherein the data collected in support of the clinical study conforms to clinical data standards that defines how the data is to be captured and mapped to underlying variable names.

Example 3. The method of any combination of examples 1 and 2, wherein determining the data collected in support of the clinical research study comprises, determining, based on a schedule of activities for a study protocol, a data collection type of the data collected in support of the clinical research trial.

Example 4. The method of example 3, wherein obtaining the first mapping comprise obtaining, based on the data collection type of the data collected in support of the clinical research trial, the first mapping between the data collected in support of the clinical research trial and the intermediate concept that uniformly classifies the data collected in support of the clinical research trial.

Example 5. The method of any combination of examples 1-4, wherein obtaining the second mapping comprises obtaining, based on metadata for the standard model, the second mappings between the intermediate concept and the standard model that conforms to the regulatory standard.

Example 6. The method of any combination of examples 1-5, further comprising: retrieving, by processing circuitry and from a regulatory database, a template based on a governance process; receiving, by the processing circuitry and via a user interface, input from a user; parameterizing, by the processing circuitry, the template based on the governance process with the user input to create a parameterized template; and storing, by the processing circuitry, the parameterized template in a database.

Example 7. The method of example 6, further comprising: generating, by the processing circuitry and based on the parameterized template, at least one study objective and at least one study endpoint for the clinical research study; generating, by the processing circuitry and based on the at least one study objective and the at least one study endpoint, a sequence of one or more study events specifying one or more study activities to be executed for the study event; and exporting, by the processing circuitry and to one or more of the regulatory database and a microservice, metadata for the clinical research study.

Example 8. The method of example 7, wherein determining the data collected in support of the clinical research study comprises, determining, based on the sequence of the one or more study events specifying the one or more study activities, a data collection type of the data collected in support of the clinical research trial.

Example 9. The method of example 8, wherein obtaining the first mapping comprises obtaining, based on the data collection type of the data collected in support of the clinical research trial, the first mapping between the data collected in support of the clinical research trial and the intermediate concept that uniformly classifies the data collected in support of the clinical research trial.

Example 10. The method of any combination of examples 7-9, wherein each study activity of the one or more study activities is selected from a group comprising at least: a clinical treatment or procedure to be performed on a subject; a data element to be measured from the subject; or non-treatment related data of the subject.

Example 11. The method of any combination of examples 6-10, wherein obtaining the second mapping comprises obtaining, based on metadata for the standard model stored to the regulatory database, the second mappings between the intermediate concept and the standard model that conforms to the regulatory standard.

Example 12. The method of any combination of examples 6-11, wherein the regulatory database comprises a metadata repository (MDR) database.

Example 13. The method of example 12, wherein the MDR database comprises one or more of an International Organization for Standardization (ISO) 11179-based MDR database, wherein the ISO 11179-based MDR database is hierarchically arranged with respect to a global organizational group containing shared template definition elements, and one or more sponsor-specific-based organizational subgroups containing sponsor-specific template definition elements, with the hierarchy facilitating reuse of the content contained within the global organizational group without compromising access limitations with respect to the sponsor-specific-based subgroups.

Example 14. The method of any combination of examples 1-13, wherein the transformational data comprises one or more of statistical analysis system (SAS) code, R code, and a specification.

Example 15. A computing system comprising: a memory configured to store a code generator; and one or more processors configured to execute the code generator, the code generator configured to: determine data collected in support of a clinical research study; obtain a first mapping between the data collected in support of the clinical study and an intermediate concept that uniformly classifies the data collected in support of the clinical research study; obtain a second mapping between the intermediate concept and a standard model that conforms to a regulatory standard; generate, based on the first mapping and the second mapping, transformational data that defines a transformation between the data collected in support of the clinical research study and data that conforms to the standard model; and output the transformational data.

Example 16. The computing system of example 15, wherein the data collected in support of the clinical study conforms to clinical data standards that defines how the data is to be captured and mapped to underlying variable names.

Example 17. The computing system of any combination of examples 15 and 16, wherein the code generator is, when configured to determine the data collected in support of the clinical research study, configured to determine, based on a schedule of activities for a study protocol, a data collection type of the data collected in support of the clinical research trial.

Example 18. The computing system of example 17, wherein the code generator is, when configured to obtain the first mapping, configured to obtain, based on the data collection type of the data collected in support of the clinical research trial, the first mapping between the data collected in support of the clinical research trial and the intermediate concept that uniformly classifies the data collected in support of the clinical research trial.

Example 19. The computing system of any combination of examples 15-18, wherein the code generator is, when configured to obtain the second mapping, configured to obtain, based on metadata for the standard model, the second mappings between the intermediate concept and the standard model that conforms to the regulatory standard.

Example 20. The computing system of any combination of examples 15-19, wherein the one or more processors are further configured to: retrieve, from a regulatory database, a template based on a governance process; receive, via a user interface, input from a user; parameterize the template based on the governance process with the user input to create a parameterized template; and store the parameterized template in a database.

Example 21. The computing system of example 20, wherein the one or more processors are further configured to: generate, based on the parameterized template, at least one study objective and at least one study endpoint for the clinical research study; generate, based on the at least one study objective and the at least one study endpoint, a sequence of one or more study events specifying one or more study activities to be executed for the study event; and export, to one or more of the regulatory database and a microservice, metadata for the clinical research study.

Example 22. The computing system of example 21, wherein the code generator is, when configured to determine the data collected in support of the clinical research study, configured to determine, based on the sequence of the one or more study events specifying the one or more study activities, a data collection type of the data collected in support of the clinical research trial.

Example 23. The computing system of example 22, wherein the code generator is, when configured to obtain the first mapping, configured to obtain, based on the data collection type of the data collected in support of the clinical research trial, the first mapping between the data collected in support of the clinical research trial and the intermediate concept that uniformly classifies the data collected in support of the clinical research trial.

Example 24. The computing system of any combination of examples 21-23, wherein each study activity of the one or more study activities is selected from a group comprising at least: a clinical treatment or procedure to be performed on a subject; a data element to be measured from the subject; or non-treatment related data of the subject.

Example 25. The computing system of any combination of examples 20-24, wherein the code generator is, when configured to obtain the second mapping, configured to obtain, based on metadata for the standard model stored to the regulatory database, the second mappings between the intermediate concept and the standard model that conforms to the regulatory standard.

Example 26. The computing system of any combination of examples 20-25, wherein the regulatory database comprises a metadata repository (MDR) database.

Example 27. The computing system of example 26, wherein the MDR database comprises one or more of an International Organization for Standardization (ISO) 11179-based MDR database, wherein the ISO 11179-based MDR database is hierarchically arranged with respect to a global organizational group containing shared template definition elements, and one or more sponsor-specific-based organizational subgroups containing sponsor-specific template definition elements, with the hierarchy facilitating reuse of the content contained within the global organizational group without compromising access limitations with respect to the sponsor-specific-based subgroups.

Example 28. The computing system of any combination of examples 15-27, wherein the transformational data comprises one or more of statistical analysis system (SAS) code, R code, and a specification.

Example 29. A non-transitory computer-readable storage medium having instructions stored thereon that, when executed, cause one or more processors to: determine data collected in support of a clinical research study; obtain a first mapping between the data collected in support of the clinical study and an intermediate concept that uniformly classifies the data collected in support of the clinical research study; obtain a second mapping between the intermediate concept and a standard model that conforms to a regulatory standard; generate, based on the first mapping and the second mapping, transformational data that defines a transformation between the data collected in support of the clinical research study and data that conforms to the standard model; and output the transformational data.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
   determining, by a code generator executed by processing circuitry, data collected in support of a clinical research study, wherein determining the data collected in support of the clinical research study comprises, determining, based on a schedule of activities for a study protocol, a data collection type of the data collected in support of the clinical research trial;
   obtaining, by the code generator, a first mapping between the data collected in support of the clinical research study and an intermediate concept that uniformly classifies the data collected in support of the clinical research study, wherein obtaining the first mapping comprise obtaining, based on the data collection type of the data collected in support of the clinical research trial, the first mapping between the data collected in support of the clinical research trial and the intermediate concept that uniformly classifies the data collected in support of the clinical research trial;

obtaining, by the code generator, a second mapping between the intermediate concept and a standard model that conforms to a regulatory standard;

generating, by the code generator and based on the first mapping and the second mapping, transformational data that defines a transformation between the data collected in support of the clinical research study and data that conforms to the standard model; and outputting, by the code generator, the transformational data.

2. The method of claim 1, wherein the data collected in support of the clinical study conforms to clinical data standards that defines how the data is to be captured and mapped to underlying variable names.

3. The method of claim 1, wherein obtaining the second mapping comprises obtaining, based on metadata for the standard model, the second mappings between the intermediate concept and the standard model that conforms to the regulatory standard.

4. The method of claim 1, further comprising:
retrieving, by processing circuitry and from a regulatory database, a template based on a governance process;
receiving, by the processing circuitry and via a user interface, input from a user;
parameterizing, by the processing circuitry, the template based on the governance process with the user input to create a parameterized template; and
storing, by the processing circuitry, the parameterized template in a database.

5. The method of claim 4, further comprising:
generating, by the processing circuitry and based on the parameterized template, at least one study objective and at least one study endpoint for the clinical research study;
generating, by the processing circuitry and based on the at least one study objective and the at least one study endpoint, a sequence of one or more study events specifying one or more study activities to be executed for the study event; and
exporting, by the processing circuitry and to one or more of the regulatory database and a microservice, metadata for the clinical research study.

6. The method of claim 5, wherein determining the data collected in support of the clinical research study comprises, determining, based on the sequence of the one or more study events specifying the one or more study activities, a data collection type of the data collected in support of the clinical research trial.

7. The method of claim 6, wherein obtaining the first mapping comprises obtaining, based on the data collection type of the data collected in support of the clinical research trial, the first mapping between the data collected in support of the clinical research trial and the intermediate concept that uniformly classifies the data collected in support of the clinical research trial.

8. The method of claim 5, wherein each study activity of the one or more study activities is selected from a group comprising at least:
a clinical treatment or procedure to be performed on a subject;

a data element to be measured from the subject; or
non-treatment related data of the subject.

9. The method of claim 4, wherein obtaining the second mapping comprises obtaining, based on metadata for the standard model stored to the regulatory database, the second mappings between the intermediate concept and the standard model that conforms to the regulatory standard.

10. The method of claim 4, wherein the regulatory database comprises a metadata repository (MDR) database.

11. The method of claim 10, wherein the MDR database comprises one or more of an International Organization for Standardization (ISO) 11179-based MDR database, wherein the ISO 11179-based MDR database is hierarchically arranged with respect to a global organizational group containing shared template definition elements, and one or more sponsor-specific-based organizational subgroups containing sponsor-specific template definition elements, with the hierarchy facilitating reuse of the content contained within the global organizational group without compromising access limitations with respect to the sponsor-specific-based subgroups.

12. The method of claim 1, wherein the transformational data comprises one or more of statistical analysis system (SAS) code, R code, and a specification.

13. A computing system comprising:
a memory configured to store a code generator; and
one or more processors configured to execute the code generator, the code generator configured to:
determine data collected in support of a clinical research study, wherein the code generator is, when configured to determine the data collected in support of the clinical research study, configured to determine, based on a schedule of activities for a study protocol, a data collection type of the data collected in support of the clinical research trial;
obtain a first mapping between the data collected in support of the clinical study and an intermediate concept that uniformly classifies the data collected in support of the clinical research study, wherein the code generator is, when configured to obtain the first mapping, configured to obtain, based on the data collection type of the data collected in support of the clinical research trial, the first mapping between the data collected in support of the clinical research trial and the intermediate concept that uniformly classifies the data collected in support of the clinical research trial;
obtain a second mapping between the intermediate concept and a standard model that conforms to a regulatory standard;
generate, based on the first mapping and the second mapping, transformational data that defines a transformation between the data collected in support of the clinical research study and data that conforms to the standard model; and
output the transformational data.

14. The computing system of claim 13, wherein the data collected in support of the clinical study conforms to clinical data standards that defines how the data is to be captured and mapped to underlying variable names.

15. The computing system of claim 13, wherein the code generator is, when configured to obtain the second mapping, configured to obtain, based on metadata for the standard model, the second mappings between the intermediate concept and the standard model that conforms to the regulatory standard.

16. The computing system of claim 13, wherein the one or more processors are further configured to:

retrieve, from a regulatory database, a template based on a governance process;
receive, via a user interface, input from a user;
parameterize the template based on the governance process with the user input to create a parameterized template; and
store the parameterized template in a database.

17. The computing system of claim 16, wherein the one or more processors are further configured to:
generate, based on the parameterized template, at least one study objective and at least one study endpoint for the clinical research study;
generate, based on the at least one study objective and the at least one study endpoint, a sequence of one or more study events specifying one or more study activities to be executed for the study event; and
export, to one or more of the regulatory database and a microservice, metadata for the clinical research study.

18. The computing system of claim 17, wherein the code generator is, when configured to determine the data collected in support of the clinical research study, configured to determine, based on the sequence of the one or more study events specifying the one or more study activities, a data collection type of the data collected in support of the clinical research trial.

19. The computing system of claim 18, wherein the code generator is, when configured to obtain the first mapping, configured to obtain, based on the data collection type of the data collected in support of the clinical research trial, the first mapping between the data collected in support of the clinical research trial and the intermediate concept that uniformly classifies the data collected in support of the clinical research trial.

20. The computing system of claim 17, wherein each study activity of the one or more study activities is selected from a group comprising at least:
a clinical treatment or procedure to be performed on a subject;
a data element to be measured from the subject; or
non-treatment related data of the subject.

21. The computing system of claim 16, wherein the code generator is, when configured to obtain the second mapping, configured to obtain, based on metadata for the standard model stored to the regulatory database, the second mappings between the intermediate concept and the standard model that conforms to the regulatory standard.

22. The computing system of claim 16, wherein the regulatory database comprises a metadata repository (MDR) database.

23. The computing system of claim 22, wherein the MDR database comprises one or more of an International Organization for Standardization (ISO) 11179-based MDR database, wherein the ISO 11179-based MDR database is hierarchically arranged with respect to a global organizational group containing shared template definition elements, and one or more sponsor-specific-based organizational subgroups containing sponsor-specific template definition elements, with the hierarchy facilitating reuse of the content contained within the global organizational group without compromising access limitations with respect to the sponsor-specific-based subgroups.

24. The computing system of claim 13, wherein the transformational data comprises one or more of statistical analysis system (SAS) code, R code, and a specification.

25. A non-transitory computer-readable storage medium having instructions stored thereon that, when executed, cause one or more processors to:
determine data collected in support of a clinical research study, wherein the instructions, when causing the one or more processors to determine the data collected in support of the clinical research study, include instructions that, when executed, cause the one or more processors to determine, based on a schedule of activities for a study protocol, a data collection type of the data collected in support of the clinical research trial;
obtain a first mapping between the data collected in support of the clinical study and an intermediate concept that uniformly classifies the data collected in support of the clinical research study, wherein the instructions that when executed cause the one or more processors to obtain the first mapping, include instructions that when executed cause the one or more processors to obtain, based on the data collection type of the data collected in support of the clinical research trial, the first mapping between the data collected in support of the clinical research trial and the intermediate concept that uniformly classifies the data collected in support of the clinical research trial;
obtain a second mapping between the intermediate concept and a standard model that conforms to a regulatory standard;
generate, based on the first mapping and the second mapping, transformational data that defines a transformation between the data collected in support of the clinical research study and data that conforms to the standard model; and
output the transformational data.

* * * * *